(12) United States Patent
Sekiguchi et al.

(10) Patent No.: US 8,471,032 B2
(45) Date of Patent: Jun. 25, 2013

(54) BENZIMIDAZOLE COMPOUND IN CRYSTAL FORM AND SALT THEREOF

(75) Inventors: Sumie Sekiguchi, Osaka (JP); Takayuki Ishige, Osaka (JP); Masanori Minoguchi, Osaka (JP); Hideki Horiuchi, Osaka (JP); Shinichirou Ono, Osaka (JP); Toshihiko Tanaka, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 13/119,242

(22) PCT Filed: Sep. 16, 2009

(86) PCT No.: PCT/JP2009/066116
§ 371 (c)(1),
(2), (4) Date: Mar. 16, 2011

(87) PCT Pub. No.: WO2010/032731
PCT Pub. Date: Mar. 25, 2010

(65) Prior Publication Data
US 2011/0178128 A1    Jul. 21, 2011

(30) Foreign Application Priority Data
Sep. 16, 2008 (JP) ................. 2008-235846

(51) Int. Cl.
*C07D 211/32* (2006.01)

(52) U.S. Cl.
USPC ........................................ 546/199

(58) Field of Classification Search
USPC ........................................ 546/199
See application file for complete search history.

(56) References Cited

U.S. PATENT DOCUMENTS

| | | | |
|---|---|---|---|
| 6,043,366 | A | 3/2000 | Adam et al. |
| 6,071,925 | A | 6/2000 | Adam et al. |
| 6,258,825 | B1 | 7/2001 | Ozaki et al. |
| 6,423,725 | B1 | 7/2002 | Ito et al. |
| 6,642,247 | B2 | 11/2003 | Adam et al. |
| 7,396,839 | B2 | 7/2008 | Niddam-Hildesheim et al. |
| 8,207,201 | B2 | 6/2012 | Teshima et al. |
| 2002/0009486 | A1 | 1/2002 | Godbey |
| 2003/0176701 | A1 | 9/2003 | Adam et al. |
| 2004/0009989 | A1 | 1/2004 | Niddam-Hildesheim et al. |
| 2005/0119308 | A1 | 6/2005 | Teshima et al. |
| 2008/0194635 | A1 | 8/2008 | Murtagh et al. |
| 2009/0076120 | A1 | 3/2009 | Takeyasu et al. |
| 2010/0069382 | A1 | 3/2010 | Teshima et al. |
| 2010/0120841 | A1 | 5/2010 | Nakano et al. |

FOREIGN PATENT DOCUMENTS

| | | |
|---|---|---|
| EP | 1 491 212 | 12/2004 |
| JP | 10-212290 | 8/1998 |
| JP | 11-228575 | 8/1999 |
| JP | 2000-26466 | 1/2000 |
| JP | 2003-519698 | 6/2003 |
| JP | 2006-508909 | 3/2006 |
| JP | 2006-199700 | 8/2006 |
| JP | 2008-534436 | 8/2008 |
| WO | 98/54168 | 12/1998 |
| WO | 99/36421 | 7/1999 |
| WO | 00/06545 | 2/2000 |
| WO | 01/39775 | 6/2001 |
| WO | 01/51919 | 7/2001 |
| WO | 03/082333 | 10/2003 |
| WO | 2004/012739 | 2/2004 |
| WO | 2005/028466 | 3/2005 |
| WO | 2006/077497 | 7/2006 |
| WO | 2006/109836 | 10/2006 |
| WO | 2008/050698 | 5/2008 |
| WO | 2008/102859 | 8/2008 |
| WO | 2008/105497 | 9/2008 |

OTHER PUBLICATIONS

International Search Report issued Oct. 13, 2009 in International (PCT) Application No. PCT/JP2009/066116.
Extended European Search Report issued Jun. 6, 2012 in corresponding European Application No. 09814576.6.
S. Byrn et al., "Pharmaceutical Solids: A Strategic Approach to Regulatory Considerations", Pharmaceutical Research, vol. 12, No. 7, pp. 945-954, 1995.
Chinese Office Action, with English translation, issued Nov. 22, 2012 in corresponding Chinese Patent Application No. 200980136325.X.

*Primary Examiner* — John Mabry
(74) *Attorney, Agent, or Firm* — Wenderoth, Lind & Ponack, L.L.P.

(57) ABSTRACT

The present invention aims to provide a stable form of (R)-2-{3-[1-(acenaphthen-1-yl)piperidin-4-yl]-2,3-dihydro-2-oxo-benzimidazol-1-yl}-N-methylacetamide, which is free of problems of water adsorption and the like, and shows superior water solubility.
The present invention provides a crystal and a salt of (R)-2-{3-[1-(acenaphthen-1-yl)piperidin-4-yl]-2,3-dihydro-2-oxo-benzimidazol-1-yl}-N-methylacetamide in a crystal form.

1 Claim, 17 Drawing Sheets

BENZIMIDAZOLE COMPOUND IN CRYSTAL FORM AND SALT THEREOF

TECHNICAL FIELD

The present invention relates to (R)-2-{3-[1-(acenaphthen-1-yl)piperidin-4-yl]-2,3-dihydro-2-oxo-benzimidazol-1-yl}-N-methylacetamide (hereinafter to be referred to as the present compound) or a salt thereof in a crystal form.

BACKGROUND ART

The present compound is represented by the following structural formula and shows an ORL-1 (opioid receptor-like 1) receptor agonistic activity (patent document 1). The present compound was produced in Example 18 of patent document 1.

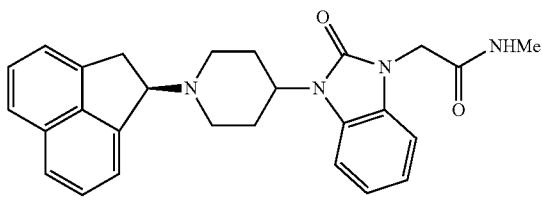 [SMILES: CNC(=O)Cn1c(=O)n(C2CCN([C@@H]3Cc4cccc5cccc3c45)CC2)c2ccccc21]

Since a compound having an ORL-1 receptor agonistic activity is useful for the treatment of a mental disorder, and neuropathy and a physiological disorder, particularly for the improvement of anxiety and stress disorder, melancholia, traumatic disorder, loss of memory due to Alzheimer's disease or other dementia, symptoms of epilepsy and convulsion, acute and/or chronic pain symptom, remission of drug withdrawal symptoms including abstinence symptoms caused by cessation of abused drug, alcohol abuse, conttol of water balance, $Na^+$ excretion, artery blood pressure disorder, eating disorders such as obesity and anorexia, and circadian rhythm sleep disorder (patent documents 1-10), the present compound is also useful for the prophylactic and/or treatment of the above-mentioned diseases.

DOCUMENT LIST

Patent Documents patent document 1: WO03/082333
patent document 2: JP-A-10-212290
patent document 3: JP-A-11-228575
patent document 4: JP-A-2000-26466
patent document 5: WO98/54168
patent document 6: WO99/36421
patent document 7: WO00/06545
patent document 8: WO01/39775
patent document 9: WO2005/028466
patent document 10: WO2008/050698

SUMMARY OF THE INVENTION

Problems to be Solved by the Invention

The problem of the present invention is to provide a stable form of the present compound, which form is free of problems such as water adsorption and the like, and shows superior water solubility.

Means of Solving the Problems

The present inventors have conducted intensive studies in an attempt to solve the aforementioned problems and found that the present compound or a salt thereof in a crystal form is a stable embodiment, since it is almost free of weight change caused by water adsorption, and that a salt of the present compound has superior water solubility, which resulted in the completion of the present invention.

Accordingly, the present invention provides the following.

[1] A salt of (R)-2-{3-[1-(acenaphthen-1-yl)piperidin-4-yl]-2,3-dihydro-2-oxo-benzimidazol-1-yl}-N-methylacetamide in a crystal form.

[2] The salt of [1], which is hydrochloride, methanesulfonate, fumarate, hydrobromide, tartrate or citrate.

[3] (R)-2-{3-[1-(acenaphthen-1-yl)piperidin-4-yl]-2,3-dihydro-2-oxo-benzimidazol-1-yl}-N-methylacetamide 1 hydrochloride 1 hydrate showing peaks at diffraction angles 2θ of about 5.6°, 16.2°, 19.0°, 20.1° and 24.9° (each ±0.2°) in powder X-ray diffraction spectrum.

[4] The 1 hydrochloride 1 hydrate of [3], which shows the powder X-ray diffraction pattern of FIG. 1 and/or the thermogravimetry/differential thermal analysis (TG/DTA) curve of FIG. 2.

[5] (R)-2-{3-[1-(acenaphthen-1-yl)piperidin-4-yl]-2,3-dihydro-2-oxo-benzimidazol-1-yl}-N-methylacetamide 1 hydrochloride showing peaks at diffraction angles 2θ of about 5.2°, 6.8°, 9.1°, 10.5° and 15.7° (each ±0.2°) in powder X-ray diffraction spectrum.

[6] The 1 hydrochloride of [5], which shows the powder X-ray diffraction pattern of FIG. 3 and/or the thermogravimetry/differential thermal analysis (TG/DTA) curve of FIG. 4.

[7] (R)-2-{3-[1-(acenaphthen-1-yl)piperidin-4-yl]-2,3-dihydro-2-oxo-benzimidazol-1-yl}-N-methylacetamide methanesulfonate showing peaks at diffraction angles 2θ of about 7.6°, 11.5°, 17.6°, 18.4°, 19.9° and 23.5° (each ±0.2°) in powder X-ray diffraction spectrum.

[8] The methanesulfonate of [7], which shows the powder X-ray diffraction pattern of FIG. 9 and/or the thermogravimetry/differential thermal analysis (TG/DTA) curve of FIG. 10.

[9] (R)-2-{3-[1-(acenaphthen-1-yl)piperidin-4-yl]-2,3-dihydro-2-oxo-benzimidazol-1-yl}-N-methylacetamide ½ fumarate 3/2 hydrate showing peaks at diffraction angles 2θ of about 8.4°, 11.2°, 18.0°, 19.2°, 21.1° and 23.1° (each ±0.2°) in powder X-ray diffraction spectrum.

[10] The ½ fumarate 3/2 hydrate of [9], which shows the powder X-ray diffraction pattern of FIG. 15 and/or the thermogravimetry/differential thermal analysis (TG/DTA) curve of FIG. 16.

[11] A crystal of (R)-2-{3-[1-(adenaphthen-1-yl)piperidin-4-yl]-2,3-dihydro-2-oxo-benzimidazol-1-yl}-N-methylacetamide showing peaks at diffraction angles 2θ of about 6.4°, 12.5°, 12.8°, 16.5°, 18.7°, 21.6° and 23.9° (each ±0.2°) in powder X-ray diffraction spectrum.

[12] The crystal of [11], which shows the powder X-ray diffraction pattern of FIG. 22 and/or the differential scanning calorimetry (DSC) curve B of FIG. 23.

[13] A crystal of (R)-2-{3-[1-(acenaphthen-1-yl)piperidin-4-yl]-2,3-dihydro-2-oxo-benzimidazol-1-yl}-N-methylacetamide showing peaks at diffraction angles 2θ of about 6.3°, 12.6°, 13.7°, 14.4°, 16.7°, 20.9° and 23.5° (each ±0.2°) in powder X-ray diffraction spectrum.

[14] The crystal of [13], which shows the powder X-ray diffraction pattern of FIG. 24 and/or the differential scanning calorimetry (DSC) curve of FIG. 25.

[15] A medicament comprising the salt or crystal of any of [1] to [14].

[16] A pharmaceutical composition comprising the salt or crystal of any of [1] to [14] as an active ingredient.

[17] The pharmaceutical composition of [16], which is used for the prophylactic and/or treatment of a disease relating to ORL-1 receptor.

[18] The pharmaceutical composition of [16], which is used for the prophylactic and/or treatment of a central nervous system disease relating to ORL-1 receptor.

[19] The pharmaceutical composition of [16], which is used for the prophylactic and/or treatment of a sleep disorder, alcohol dependence, drug dependence, anxiety or stress disorder.

[20] Use of the salt or crystal of any of [1] to [14] for the production of a prophylactic and/or therapeutic drug for a disease relating to ORL-1 receptor.

[21] Use of the salt or crystal of any of [1] to [14] for the production of a prophylactic and/or therapeutic drug for a central nervous system disease relating to ORL-1 receptor.

[22] Use of the salt or crystal of any of [1] to [14] for the production of a prophylactic and/or therapeutic drug for a sleep disorder, alcohol dependence, drug dependence, anxiety or a stress disorder.

[23] A method for the prophylaxis and/or treatment of a disease relating to ORL-1 receptor, comprising administering an effective amount of the salt or crystal of any of [1] to [14] to a subject.

[24] A method for the prophylaxis and/or treatment of a central nervous system disease relating to ORL-1 receptor, comprising administering an effective amount of the salt or crystal of any of [1] to [14] to a subject.

[25] A method for the prophylaxis and/or treatment of a sleep disorder, alcohol dependence, drug dependence, anxiety or a stress disorder, comprising administering an effective amount of the salt or crystal of any of [1] to [14] to a subject.

DESCRIPTION OF EMBODIMENTS

Figure 1:
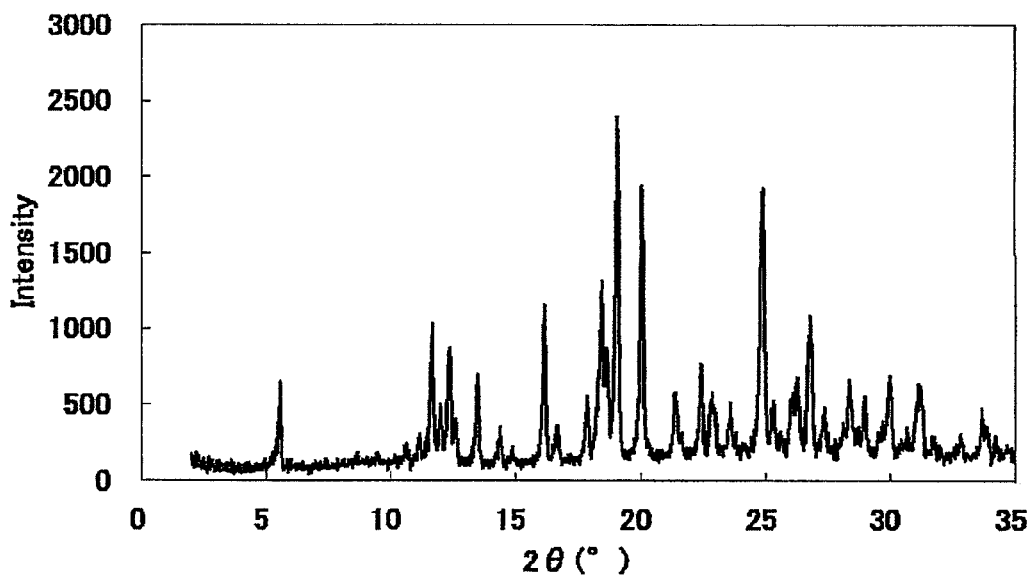
FIG. 1 is a drawing showing the XRD pattern of the present compound 1 hydrochloride 1 hydrate of Example 1.

Examples of the salt of the present compound in a crystal form include hydrochloride, methanesulfonate, fumarate, hydrobromide, tartrate, citrate and the like. These salts can be present in both forms of nonsolvate and solvate. Examples of the solvate include solvates with water, methanol, ethanol, isopropyl alcohol, acetone, acetonitrile, ethyl acetate or the like. From the aspects of pharmaceutical ingredient, hydrate is more preferable than solvate with an organic solvent. In addition, according to the number of the solvents for the present compound, solvates of hemi-, mono-, di-, tri-, tetra-, penta-, hexa- and the like can be present. In the case of a hydrate, preferred is a hydrate of not more than 3, more preferably 1 or 2 hydrate.

Examples of the salt of the present compound in a crystal form include hydrochloride 1 hydrate, hydrochloride anhydride, hydrochloride 2-3 hydrate, Type I crystal of hydrochloride 1 acetonitrilate, Type II crystal of the same, methanesulfonate anhydride, methanesulfonate 3 hydrate, methanesulfonate 2 hydrate, methanesulfonate ½-1 hydrate, ½ fumarate 3/2 hydrate, 1 fumarate 1-2 hydrate, hydrobromide, ½ DL-tartrate ½ hydrate, ½ citrate, 1 citrate, ½ DL-tartrate ½ hydrate and the like. Of these, preferred are hydrochloride 1 hydrate, hydrochloride anhydride, methanesulfonate anhydride and the like, particularly preferred is hydrochloride 1 hydrate.

The salt of the present compound in a crystal form is stable, and provides a remarkably superior effect of extremely high water solubility. Particularly, hydrochloride 1 hydrate, hydrochloride anhydride, and methanesulfonate anhydride are free of problems of water adsorption and the like, show no charging characteristics, and good flowability, and also exhibit a superior effect of high bioavailability (biological availability) by oral administration.

The salt of the present compound in a crystal form can be obtained by mixing the present compound (equivalent) with excess organic acid or inorganic acid such as hydrochloric acid, methanesulfonic acid, fumaric acid, hydrobromic acid, tartaric acid, citric acid and the like to produce a salt, and crystallizing the salt. While the solvent to be used for production of the salt may be any, one that can be used as a solvent for the subsequent crystallization is preferably selected. Examples of the solvent include water, alcohol (methanol, ethanol, 1-propanol, isopropyl alcohol, butanol etc.), ketone (acetone, methylethyl ketone etc.), nitrile (acetonitrile, propionitrile etc.), ester (ethyl formate, ethyl acetate, isopropyl acetate etc.), ether (diethyl ether, diisopropyl ether, t-butyl methyl ether, 1,4-dioxane, THF etc.), amide (formamide, N,N-dimethylformamide, N,N-dimethylacetamide etc.), halogenated hydrocarbon (dichloromethane, chloroform, 1,2-dichloroethane etc.), hydrocarbon (n-hexane, cyclohexane, benzene, toluene etc.), sulfoxide (dimethyl sulfoxide etc.) and the like, a mixed solvent thereof and the like.

Hydrochloride 1 hydrate can be produced by, for example, producing hydrochloride in a mixed solvent of an organic solvent such as alcohol (methanol, ethanol, 1-propanol, isopropyl alcohol etc.), ketone (acetone, methylethyl ketone etc.) and the like and water, and crystallizing the hydrochloride. For crystallization, ester (ethyl formate, ethyl acetate, isopropyl acetate etc.) may be added, which improves the yield.

Hydrochloride anhydride can be produced by, for example, producing hydrochloride in an organic solvent not containing water, such as alcohol (methanol, ethanol, 1-propanol, isopropyl alcohol etc.), ketone (acetone, methylethyl ketone etc.) and the like, and crystallizing the hydrochloride. In addition, when hydrochloride is produced under aqueous conditions, crystallization may be performed under anhydrous conditions provided by using azeotropic distillation, dehydrating agent and the like.

Methanesulfonate anhydride can be produced by, for example, producing methanesulfonate in an organic solvent not containing water such as alcohol (methanol, ethanol, 1-propanol, isopropyl alcohol etc.), ketone (acetone, methylethyl ketone etc.) and the like, and crystallizing the methanesulfonate. In addition, methanesulfonate anhydrate can also be produced by producing methanesulfonate under aqueous conditions, forming anhydrous conditions by using azeotropic distillation, dehydrating agent etc., and crystallizing the methanesulfonate.

Examples of the present compound in a crystal form include type I crystal, type II crystal, type III crystal, type IV (1 hydrate) crystal and type V crystal. Preferred are type I crystal and type II crystal.

The present compound can be crystallized by, for example, dissolving the present compound by heating, and cooling to allow crystallization, or adding a poor solvent to the solution of the present compound. Examples of the solvent to be used include water, alcohol (methanol, ethanol, 1-propanol, isopropyl alcohol, butanol etc.), ketone (acetone, methylethyl ketone etc.), nitrile (acetonitrile, propionitrile etc.), ester (ethyl formate, ethyl acetate, isopropyl acetate etc.), ether (diethyl ether, diisopropyl ether, t-butyl methyl ether, 1,4-dioxane, THF etc.), amide (formamide, N,N-dimethylformamide, N,N-dimethylacetamide etc.), halogenated hydrocarbon (dichloromethane, chloroform, 1,2-dichloroethane etc.), hydrocarbon (n-hexane, cyclohexane, benzene, toluene etc.), sulfoxide (dimethyl sulfoxide etc.) and the like, a mixed solvent thereof and the like. Particularly preferable examples of the solvent include water, a mixed solvent of water and alcohol (methanol, ethanol, 1-propanol, isopropyl alcohol etc.), a mixed solvent of water and ketone (acetone, methylethyl ketone etc.), a mixed solvent of these and ester (ethyl formate, ethyl acetate, isopropyl acetate etc.) and the like.

Using the present compound or a salt thereof in a crystal form of the present invention, a pharmaceutical preparation for the aforementioned prophylactic and/or therapeutic drugs (e.g., prophylactic and/or therapeutic drug for a disease relating to ORL-1 receptor (particularly central nervous system diseases), particularly, prophylactic and/or therapeutic drug for sleep disorder, alcohol dependence, drug dependence, anxiety and stress disorder) can be produced almost free of problems during production such as contamination with impurity and the like. Examples of the pharmaceutical preparation include those described in WO03/082333 and WO2008/050698, and the like, which are produced and administered according to the methods described in the publications. The dose is determined depending on the age, body weight, general health condition, sex, diet, administration time, administration method, clearance rate, drug combination and the disease state for which patients are under treatment at that time, and in consideration thereof or other factors. The daily dose is, for example, 0.01-1000 mg/kg body weight/day by oral administration, which is given in one to several portions a day, and it is about 0.01-100 mg/kg body weight/day by parenteral administration, which is given in one to several portions a day. In the present specification, the "prophylactic drug" is a drug to be administered to a healthy person who has not developed a disease and is, for example, a drug to be administered for the purpose of preventing the onset of a disease. The "therapeutic drug" is a drug to be administered to a person diagnosed by a doctor to have developed a disease (patient) and is, for example, a drug to be administered for the purpose of alleviating a disease or symptom, or recovering health. Even when the object of administration is prevention of aggravation of a disease or symptom, or prevention of attack, as long as it is administered to a patient, it is a therapeutic drug.

EXAMPLES

The present compound was synthesized according to the method described in WO03/082333.

By powder X-ray diffraction (XRD), the range of the diffraction angle 2θ of 2 to 35° was measured using a powder X-ray diffraction apparatus RINT2200/Ultima+ (RIGAKU), or X'Pert Pro MPD (PANalytical) at room temperature using Cu Kα1 as an X-ray tube. The measurement conditions for each diffraction apparatus used were as described below.

diffraction apparatus: RINT2200/Ultima+ (RIGAKU)
tube current: 40 mA, tube voltage: 40 kV, scan speed: 4°/min diffraction apparatus: X'Pert Pro MPD (PANalytical)

[condition 1] tube current: 40 mA, tube voltage: 45 kV, scan speed: 40.1°/min

[condition 2] tube current: 30 mA, tube voltage: 40 kV, scan speed: 12.3°/min

While 2θ value generally shows a variation of about ±0.2°, a larger error may be caused by measurement conditions and the like.

The thermal analysis was performed using Thermogravimetry/Differential Thermal analyzer TG/SDTA851e (TG/DTA) (Mettler Toledo), or differential scanning calorimeter DSC821e (DSC), in a dry nitrogen gas stream at 40 mL/min under temperature rise rate of 10° C./min.

Example 1

The Present Compound 1 Hydrochloride 1 Hydrate

1 Hydrochloride 1 hydrate was obtained according to the following (1)-(4).

(1) To a suspension of the present compound (2.5 g) in acetonitrile (80 ml) was added dropwise a hydrogen chloride solution [1.23 equivalents, a solution obtained by diluting 4M hydrochloric acid-ethyl acetate solution (10 ml) with acetonitrile (30 ml), 7 ml] with stirring at 40° C. The mixture was further stirred at 40° C. for 10 min to give a clear solution, which was left standing for 6 hr. Type I crystals (2.6 g) of the precipitated present compound 1 hydrochloride 1 acetonitrilate were collected by filtration. The collected crystals were dissolved in methanol (40 ml), and methanol was evaporated under reduced pressure. Aqueous acetone (10 ml, acetone 9 ml+water 1 ml) was added to give a clear solution, which was left standing for 2 days. The precipitated crystals were collected by filtration, and dried at 60° C. for 2 hr under vacuum to give the title compound (2.2 g) as white crystals.

(2) To a suspension of the present compound (37 g) in acetone (400 ml) and water (40 ml) was added dropwise 6M hydrochloric acid (15 ml, 1.07 equivalents) with stirring at room temperature. The mixture was stirred at 60° C. to give a clear solution, allowed to cool to room temperature to allow precipitation of hydrochloride. After confirmation, ethyl acetate (100 ml) was added dropwise with stirring at room temperature. After stirring at room temperature for 1 hr, ethyl acetate (100 ml) was further added dropwise, and then the mixture was stirred at room temperature for 4 hr. The precipitated crystals were collected by filtration, and dried at 70° C. for 3 hr under vacuum to give the title compound (31 g) as white crystals.

(3) To a suspension of the present compound (138.03 g), acetone (1518 ml) and water (152 ml) was added 6M hydrochloric acid (54.83 ml, 1.05 equivalents) under stirring at room temperature. After raising the inside temperature to 48° C., the insoluble material was filtered off, and the filtrate was stirred at room temperature. 30 Min later (inside temperature 40° C.), seed crystals (0.2 g) were added. After stirring at room temperature for 3 hr, isopropyl acetate (373 ml) was added at inside temperature 5-10° C., and 1 hr later, 373 ml thereof was added dropwise. After standing overnight, the mixture was filtered, washed with cool acetone (180 ml×2), and dried at 60° C. for 5 hr to give a white powder (118.83 g). This powder was left standing in a desiccator (relative humidity: ~750) for 42 hr in the presence of saturated brine to give a white powder (120.04 g).

(4) To a suspension of the present compound (1.0 g), 1-propanol (6.9 ml) and water (1.2 ml) was added concentrated hydrochloric acid (1.1 equivalents, 0.26 g) at room temperature and the mixture was stirred. The obtained clear solution was concentrated under reduced pressure to about half amount at 55° C., and isopropyl acetate (5 ml) was added dropwise by portions over 30 min. The obtained suspension was stirred at 55° C. for 1.5 hr and at room temperature for 3 hr, and the precipitated crystals were collected by filtration and dried at 60° C. under vacuum to give the title compound (1.0 g) as white crystals.

[XRD (Diffraction Apparatus: RINT2200/Ultima+)]

The XRD pattern is shown in FIG. 1. The characteristic peaks were found at diffraction angles 2θ of about 5.6°, 16.2°, 19.0°, 20.1° and 24.9° (each ±0.2°).

[TG/DTA]

Figure 2:
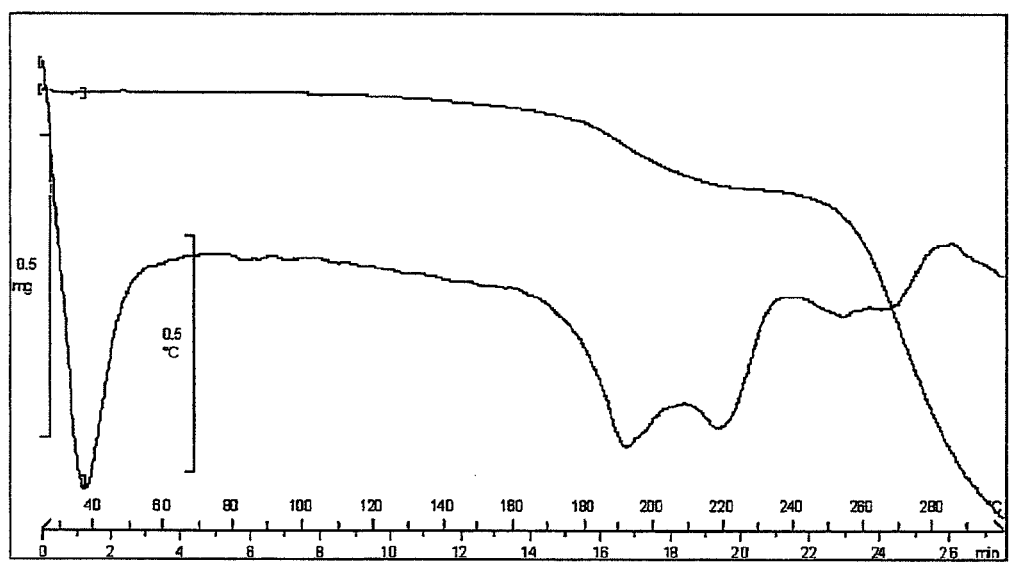
FIG. 2 is a drawing showing the TG/DTA curve of the present compound 1 hydrochloride 1 hydrate of Example 1.

A 3.6% weight decrease due to the dissociation of crystallization water, and an endothermic peak derived is therefrom were gradually observed from around 120° C. The temperature at which a weight decrease due to the dissociation of crystallization water and an endothermic peak derived therefrom occur and the range thereof in the present measurement method may vary depending on the particle size, crystal habit and the like of the crystal of the title compound. In addition, an endothermic peak having a peak top at around 220° C. was noted, and thereafter a remarkable weight decrease due to decomposition was observed. The obtained TG/DTA curve is shown in FIG. 2.

Example 2

The Present Compound 1 Hydrochloride Anhydride

To a suspension of the present compound (2.64 g) and isopropyl alcohol (29 ml) was added 6M hydrochloric acid (1.04 ml, 1.05 equivalents) with stirring at room temperature. After heating, the insoluble material was filtered off, and to the filtrate was added isopropyl alcohol (32 ml), and the mixture was continuously stirred at room temperature. The solvent (35 ml thereof) was evaporated by normal pressure distillation (removal of water by azeotropic distillation), and the seed crystals were added. The solvent (15 ml) was further evaporated, and "isopropyl alcohol (25 ml) was added and a solvent (25 ml) was evaporated" was repeated twice. After cooling to room temperature, the precipitated crystals were collected by filtration, washed with isopropyl alcohol, and dried at 60° C. for 4 hr to give a white powder (2.624 g). This powder was left standing in a desiccator (relative humidity: ~75%) for 24 hr in the presence of saturated brine to give a crystalline white powder (2.627 g).

[XRD (Diffraction Apparatus: RINT2200/Ultima+)]

Figure 3:
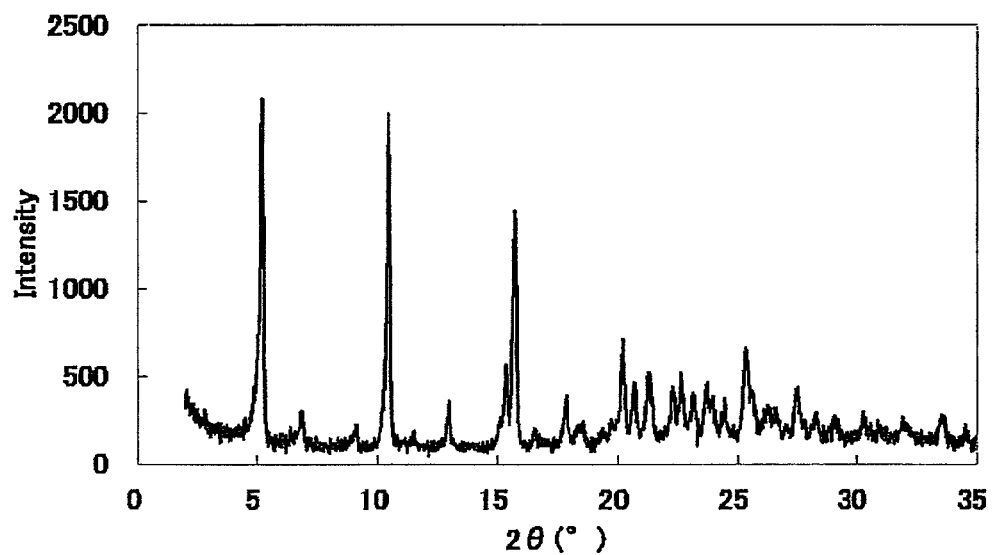
FIG. 3 is a drawing showing the XRD pattern of the present compound 1 hydrochloride of Example 2.

The XRD pattern is shown in FIG. 3. The characteristic peaks are shown at diffraction angles 2θ of about 5.2°, 6.8°, 9.1°, 10.5° and 15.7° (each ±0.2°).

[TG/DTA]

Figure 4:
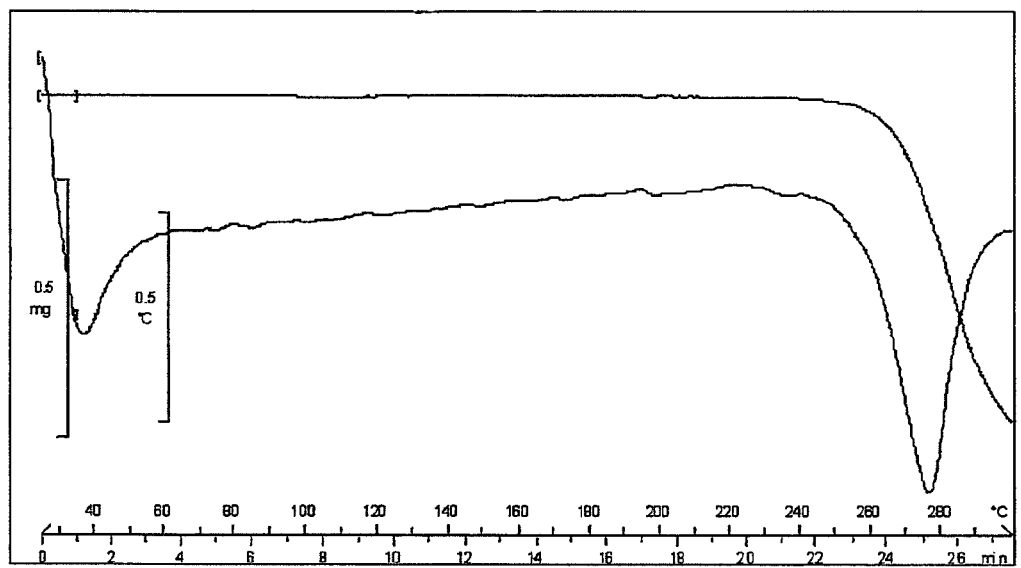
FIG. 4 is a drawing showing the TG/DTA curve of the present compound 1 hydrochloride of Example 2.

The melting and/or decomposition peak was found at 259° C. (extrapolation starting temperature), and a remarkable weight decrease due to decomposition was observed. The obtained TG/DTA curve is shown in FIG. 4.

Example 3

The Present Compound 1 Hydrochloride 2-3 Hydrates

To the 1 hydrochloride 1 hydrate (500 mg) of Example 1 was added water (15 mL), and the mixture was heated to about 75° C., and again cooled to around room temperature. To this suspension were added seed crystals, and the mixture was stirred and washed in the suspension under shading at room temperature for 1 week. The precipitated crystals were collected by filtration to give the title compound as a crystalline white powder.

[XRD (Diffraction Apparatus: RINT2200/Ultima+)]

Figure 5:
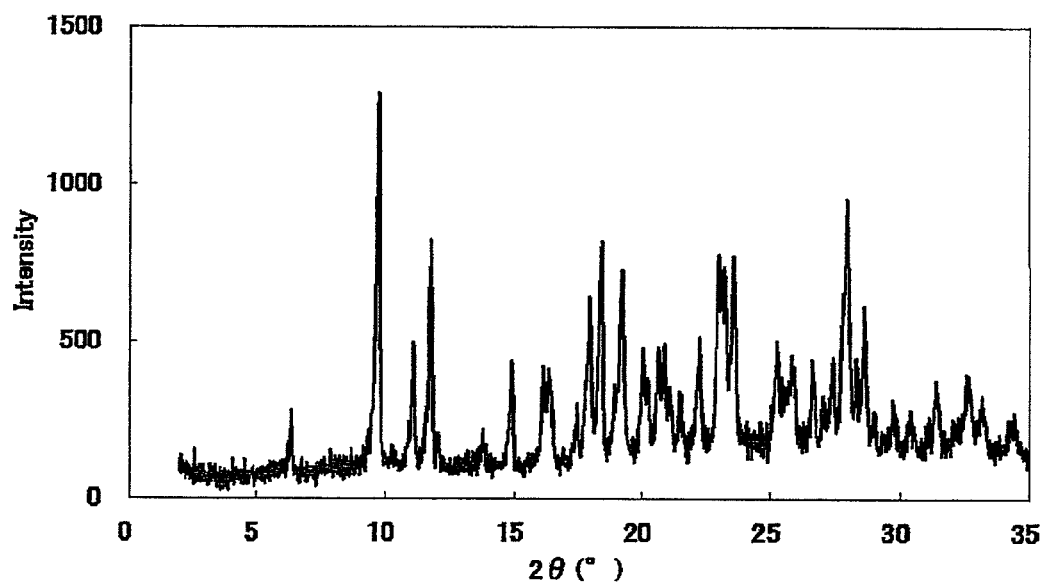
FIG. 5 is a drawing showing the XRD pattern of the present compound 1 hydrochloride 2-3 hydrate of Example 3.

The XRD pattern is shown in FIG. 5. The characteristic peaks are shown at diffraction angles 2θ of about 6.4°, 9.7°, 11.8°, 14.9°, 18.4° and 19.2° (each ±0.2°).

[TG/DTA]

Figure 6:
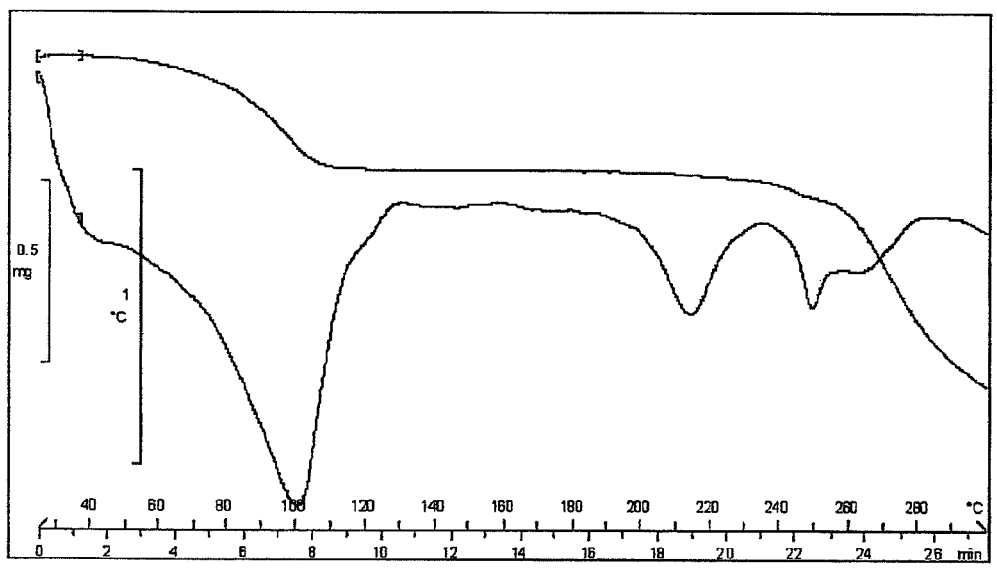
FIG. 6 is a drawing showing the TG/DTA curve of the present compound 1 hydrochloride 2-3 hydrate of Example 3.

A weight decrease due to the dissociation of crystallization water (about 7-11%, depending on environment humidity in measurement), and an endothermic peak derived therefrom were observed from around 40° C. The temperature at which a weight decrease due to the dissociation of crystallization water and an endothermic peak derived therefrom occur and the range thereof in the present measurement method may vary depending on the particle size, crystal habit and the like of the crystal of the title compound. In addition, an endothermic peak having a peak top at around 215° C. was noted, and thereafter a remarkable weight decrease due to decomposition was observed. The obtained TG/DTA curve is shown in FIG. 6.

Example 4

Type I Crystal of the Present Compound 1 Hydrochloride 1 Acetonitrilate

To the present compound (400 mg) was added 90% acetonitrile solution (1.1 ml), and the mixture was heated to 65° C. To the stirred suspension was added a hydrogen chloride-ethanol solution corresponding to 1.2 equivalents, and the mixture was completely dissolved and slowly cooled to 25° C. Thereto were added seed crystals, and the mixture was stirred at room temperature for one night and one day. The precipitated crystals were collected by filtration to give the title compound (361 mg) as a crystalline white powder.

[XRD (Diffraction Apparatus: RINT2200/Ultima+)]

Figure 7:
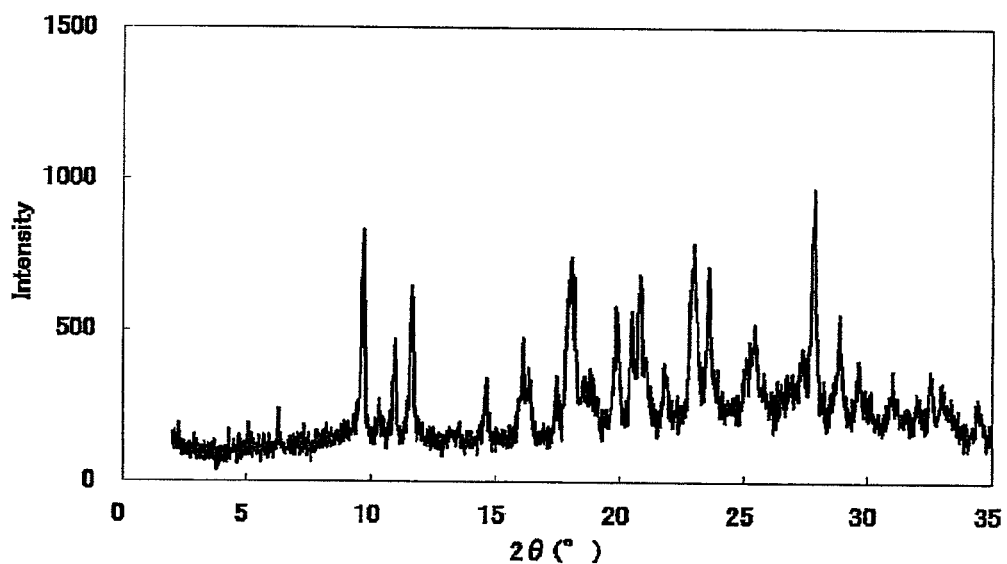
FIG. 7 is a drawing showing the XRD pattern of type I crystal of the present compound 1 hydrochloride 1 acetonitrilate of Example 4.

The XRD pattern is shown in FIG. 7. The characteristic peaks were shown at diffraction angles 2θ of about 9.7°, 18.1°, 21.9°, 25.6° and 27.8° (each ±0.2°).

Example 5

Type II Crystal of the Present Compound 1 Hydrochloride 1 Acetonitrilate

To the 1 hydrochloride 1 hydrate (5 mg) of Example 1 was added acetonitrile (2.2 mL), and the mixture was dissolved by heating to 60° C. This was filtered while hot and the filtrate was left standing at 20° C. for one night and one day to give a crystalline white solid.

[XRD (Diffraction Apparatus: X'Pert Pro MPD [Condition 2])]

Figure 8:
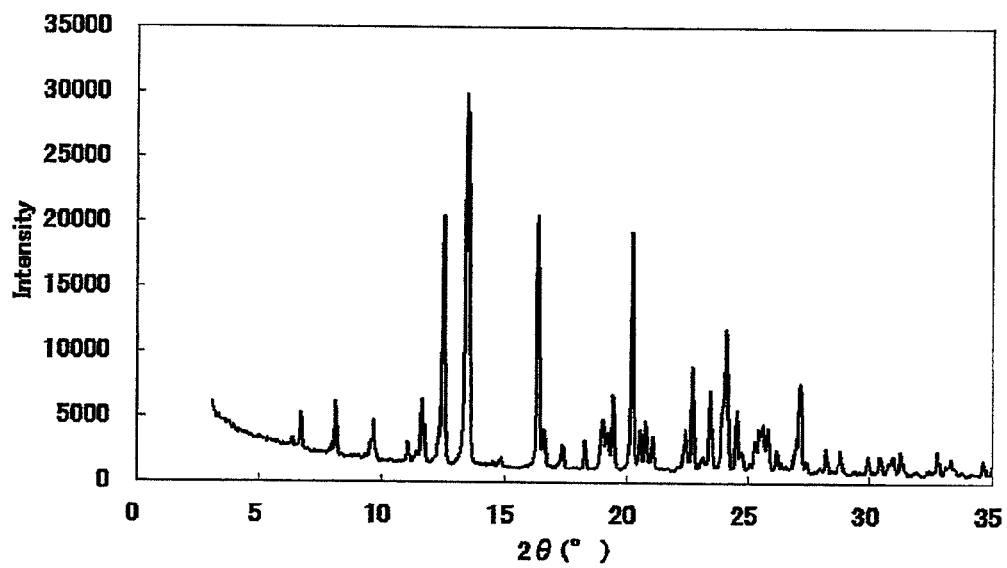
FIG. 8 is a drawing showing the XRD pattern of type II crystal of the present compound 1 hydrochloride 1 acetonitrilate of Example 5.

The XRD pattern is shown in FIG. 8. The characteristic peak were found at diffraction angles 2θ of about 12.6°, 13.6°, 16.5°, 20.3° and 24.1° (each ±0.2°).

Example 6

The Present Compound 1 Methanesulfonate Anhydride

According to the following (1) and (2), 1 methanesulfonate anhydride was obtained.

(1) To a suspension of the present compound (2 g) and aqueous ethanol (5 ml, ethanol 4.5 ml+water 0.5 ml) was added dropwise 1M methanesulfonic acid-ethanol solution (5.4 ml, 1.2 equivalents) while stirring with heating at 70° C. After complete dissolution, the mixture was cooled to room temperature, and then stirred for one night and one day. The precipitated crystals were collected by filtration, and dried at 50° C. for 10 hr under vacuum to give the title compound (1.54 g) as white crystals.

(2) To a suspension of the present compound (18 g) and methanol (300 ml) was added dropwise a solution of methanesulfonic acid (4.68 g, 1.2 equivalents) in methanol (45 ml) with stirring at room temperature. Methanol was evaporated under reduced pressure, and aqueous acetone (60 ml, acetone 54 ml+water 6 ml) was added to give a clear solution, which was left standing for 2 days. The precipitated crystals were collected by filtration, and dried at 60° C. for 4 hr under vacuum to give the title compound (11.5 g) as white crystals.

[XRD (Diffraction Apparatus: RINT2200/Ultima+)]

Figure 9:
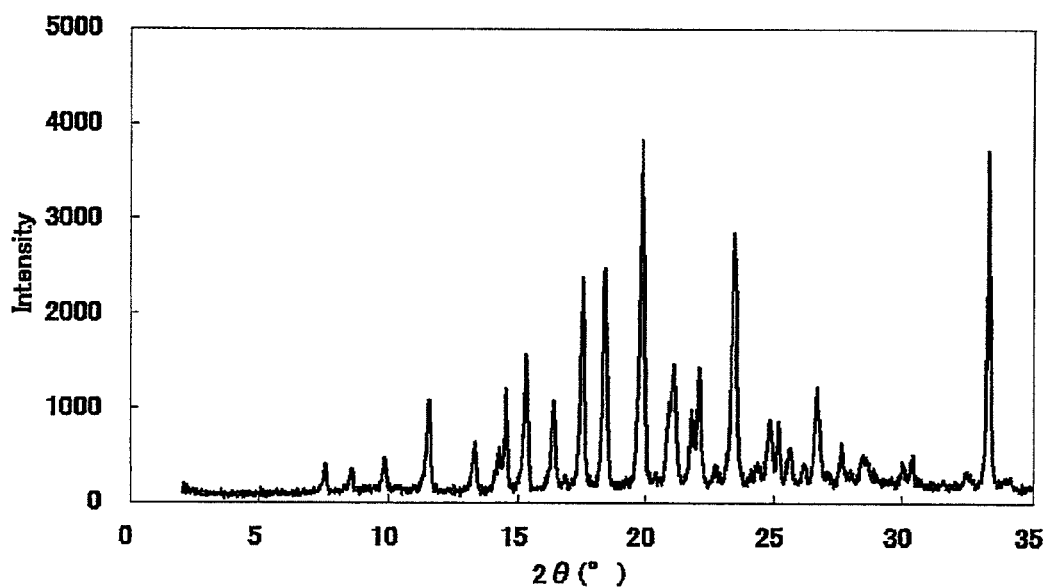
FIG. 9 is a drawing showing the XRD pattern of the present compound 1 methanesulfonate of Example 6.

The XRD pattern is shown in FIG. 9. The characteristic peaks were found at diffraction angles 2θ of about 7.6°, 11.5°, 17.6°, 18.4°, 19.9° and 23.5° (each ±0.2°).

[TG/DTA]

Figure 10:
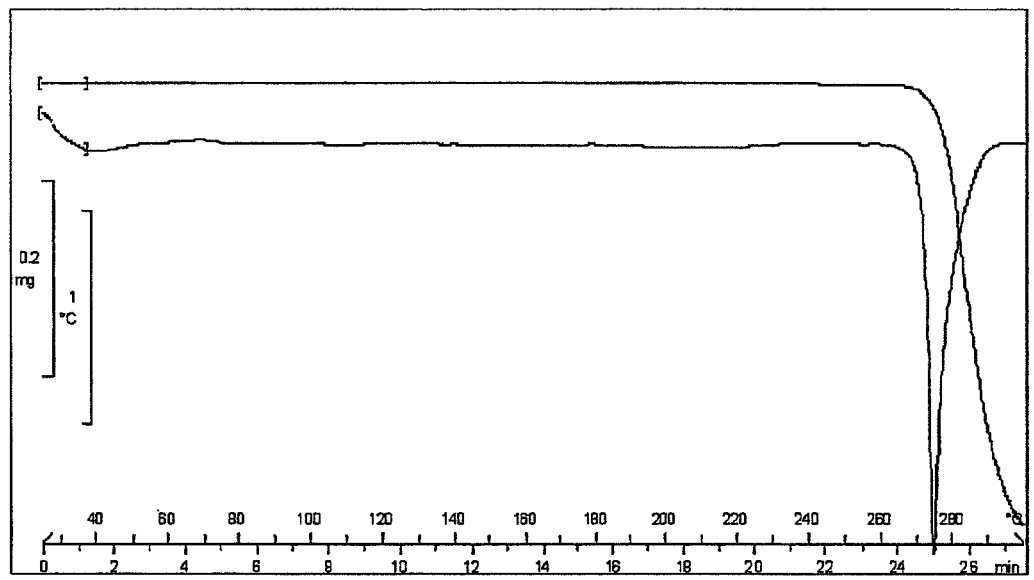
FIG. 10 is a drawing showing the TG/DTA curve of the present compound 1 methanesulfonate of Example 6.

The melting and/or decomposition peak was noted at 271° C. (extrapolation starting temperature), and a remarkable weight decrease due to decomposition was observed. The obtained TG/DTA curve is shown in FIG. 10.

Example 7

The Present Compound 1 Methanesulfonate ½-1 Hydrate

To the present compound 1 methanesulfonate anhydride (15 mg) was added a 90% toluene/methanol solution (0.1 ml). After capping, the mixture was stirred at room temperature for about 1 month under shading, and the solvent was gradually evaporated to give the title compound as a crystalline white powder.

[XRD (Diffraction Apparatus: RINT2200/Ultima+)]

Figure 11:
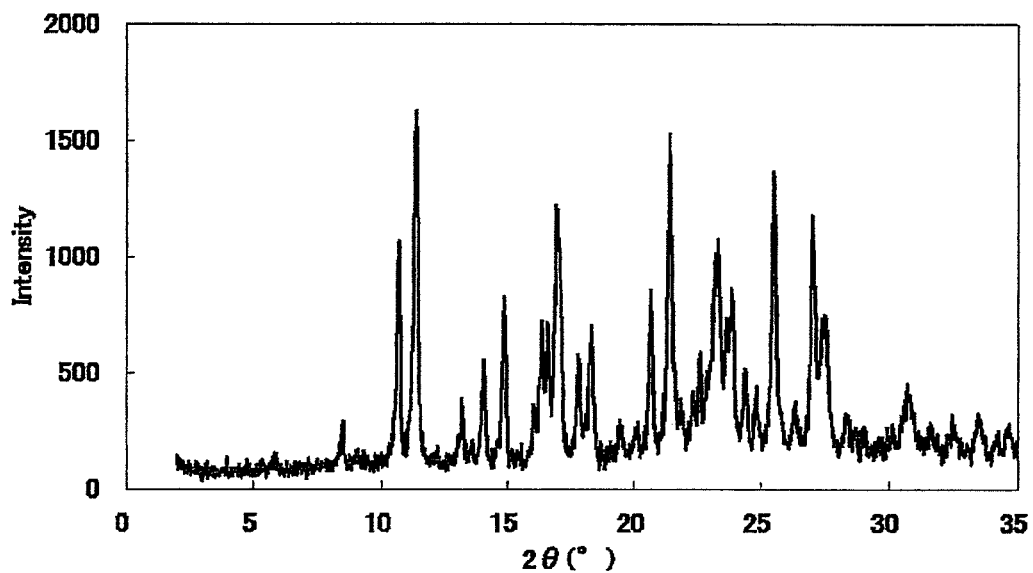
FIG. 11 is a drawing showing the XRD pattern of the present compound 1 methanesulfonate ½-1 hydrate of Example 7.

The XRD pattern is shown in FIG. 11. The characteristic peaks were found at diffraction angles 2θ of about 10.7°, 11.4°, 16.9°, 21.4° and 25.5° (each ±0.2°).

[TG/DTA]

Figure 12:
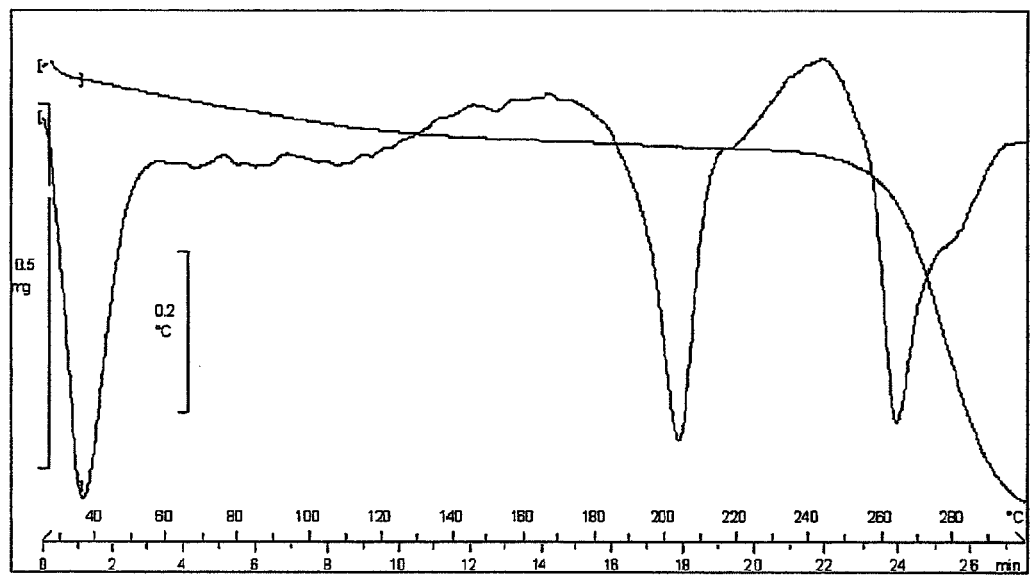
FIG. 12 is a drawing showing the TG/DTA curve of the present compound 1 methanesulfonate ½-1 hydrate of Example 7.

A 2.9% weight decrease due to the dissociation of crystallization water, and a slowly endothermic peak derived therefrom were observed from around 30° C. The temperature at which a weight decrease due to the dissociation of crystallization water and an endothermic peak derived therefrom occur and the range thereof in the present measurement method may vary depending on the particle size, crystal habit and the like of the crystal of the title compound. In addition, an endothermic peak at around 192° C. (extrapolation starting temperature) was noted, and thereafter remarkable weight decreases due to an exothermic peak and decomposition were observed. The obtained TG/DTA curve is shown in FIG. 12.

Example 8

The Present Compound 1 Methanesulfonate 3 Hydrate

Figure 13:
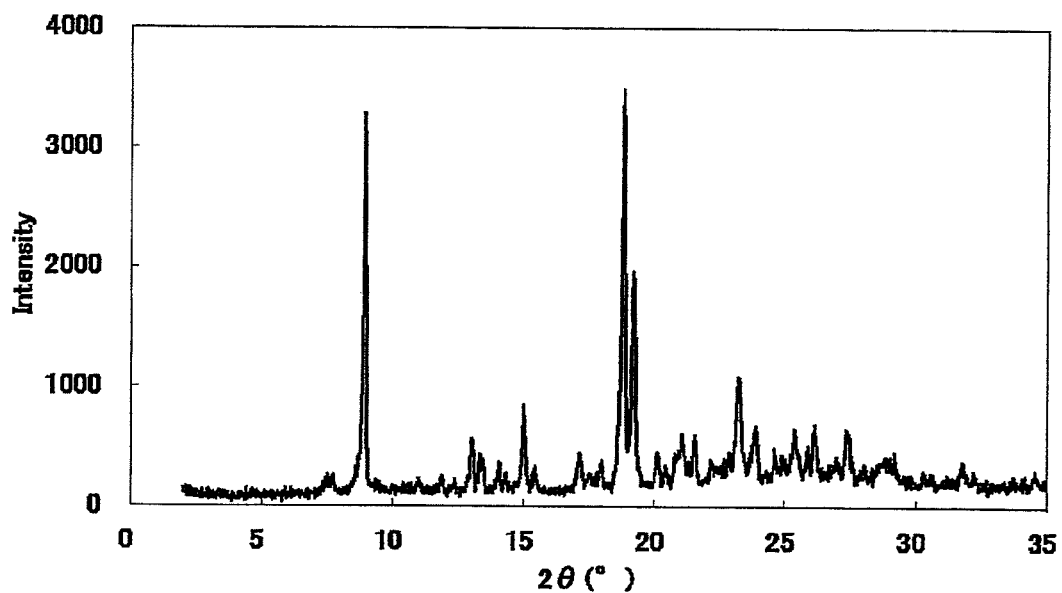
FIG. 13 is a drawing showing the XRD pattern of the present compound 1 methanesulfonate 3 hydrate of Example 8.

To the present compound 1 methanesulfonate anhydride (200 mg) was added water (2 mL). The mixture was dissolved by heating at 80° C., and cooled to room temperature. A small amount of seed crystals was added thereto, and the mixture was stirred at room temperature. The mixture became clouded. The mixture was capped and matured under shading at room temperature for 4 days, and the precipitate was collected by filtration and placed in a closed container to give the title compound as a crystalline white solid.
[XRD (Diffraction Apparatus: RINT2200/Ultima+)]
The XRD pattern is shown in FIG. 13. The characteristic peaks were found at diffraction angles 2θ of about 8.9°, 15.0°, 18.8° and 19.2° (each ±0.2°).

Example 9

Present Compound 1 Methanesulfonate 2 Hydrate

Figure 14:
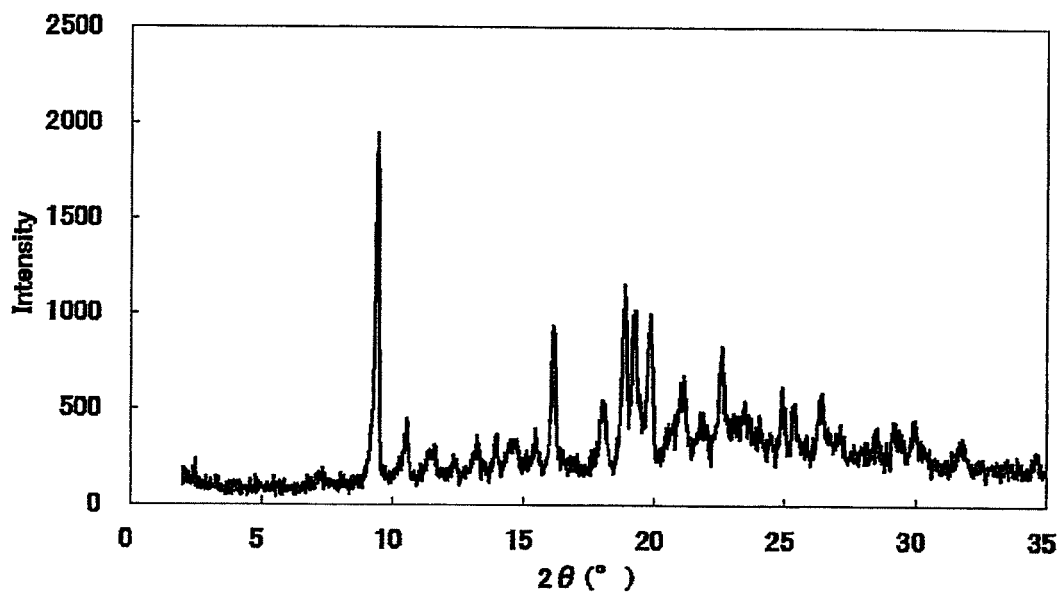
FIG. 14 is a drawing showing the XRD pattern of the present compound 1 methanesulfonate 2 hydrate of Example 9.

The present compound 1 methanesulfonate 3 hydrate of Example 8 was dried under reduced pressure at room temperature for about 30 min to give the title compound as a crystalline white powder.
[XRD (Diffraction Apparatus: RINT2200/Ultima+)]
The XRD pattern is shown in FIG. 14. The characteristic peaks were found at diffraction angles 2θ of about 9.4°, 10.6% 16.1°, 18.1° and 19.8° (each ±0.2°).

Example 10

Present Compound ½ Fumarate 3/2 Hydrate

Figure 15:
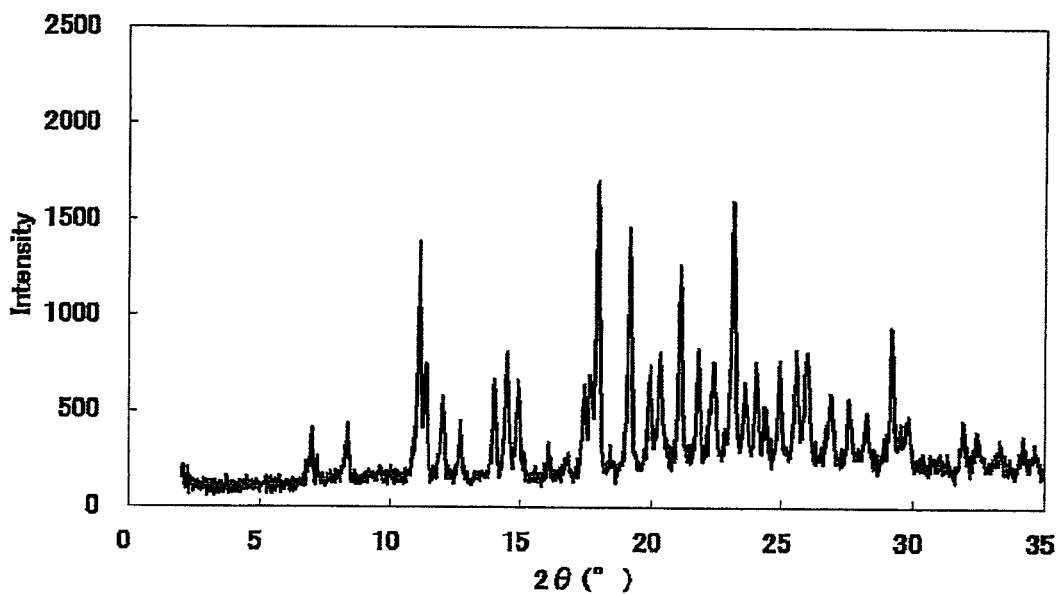
FIG. 15 is a drawing showing the XRD pattern of the present compound ½ fumarate 3/2 hydrate of Example 10.
Figure 16:
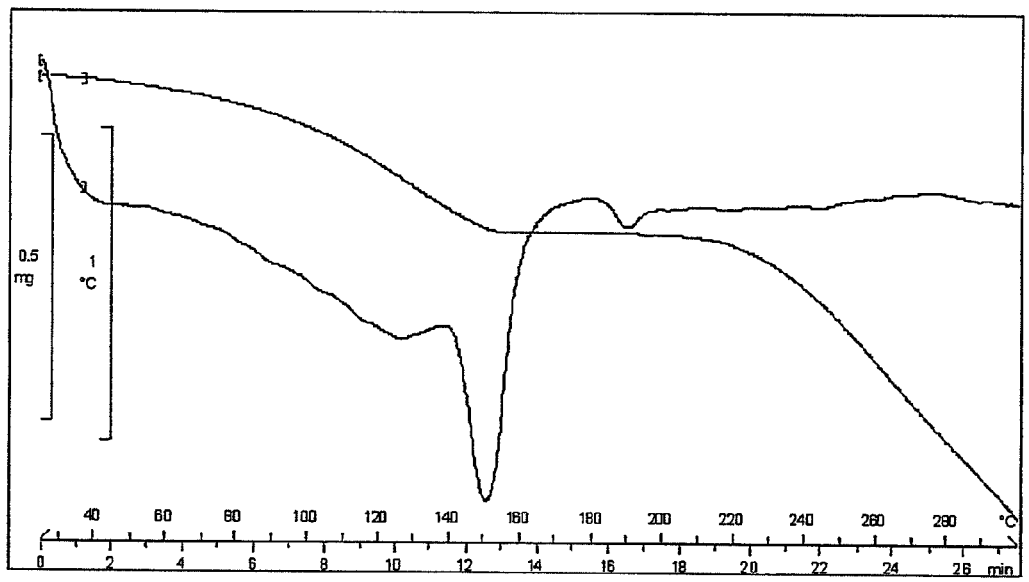
FIG. 16 is a drawing showing the TG/DTA curve of the present compound ½ fumarate 3/2 hydrate of Example 10.

To a suspension of the present compound (2 g) and aqueous ethanol (20 ml, ethanol 18 ml+water 2 ml) was added dropwise 0.5M fumaric acid-ethanol solution (10.8 ml, 1.2 equivalents) while stirring with heating at 70° C. After complete dissolution, the mixture was cooled to room temperature, and directly stirred for one night and one day. The precipitated crystals were collected by filtration, and dried at 40° C. for 2 hr under vacuum to give the title compound (1.52 g) as white crystals.
[Powder X-Ray Diffraction (XRD) Analysis]
The XRD pattern is shown in FIG. 15. The characteristic peaks were found at diffraction angles 2θ of about 8.4°, 11.2°, 18.0°, 19.2°, 21.1° and 23.1° (each ±0.2°).
[TG/DTA]
A 5.5% weight decrease due to the dissociation of crystallization water, and a slowly endothermic peak derived therefrom were gradually observed from around 50° C. The temperature at which a weight decrease due to the dissociation of crystallization water and an endothermic peak derived therefrom occur and the range thereof in the present measurement method may vary depending on the particle size, crystal habit and the like of the crystal of the title compound. In addition, an endothermic peak having a peak top at around 150° C. was noted, and a remarkable weight decrease due to decomposition was observed from around 220° C. The obtained TG/DTA curve is shown in FIG. 16.

Example 11

Present Compound 1 Fumarate 1-2 Hydrate

To the present compound (200 mg) was added methanol (2 mL), and a fumaric acid-ethanol solution corresponding to 2.4 equivalents was added dropwise under stirring with heating at 60° C. While stirring at temperature 65° C., methanol (0.9 mL) was added and the mixture was completely dissolved. By slowly cooling to room temperature, a small amount of the precipitate was observed. The mixture was stirred as it was at room temperature for about 4 days to mature the crystals, and the precipitated crystals were collected by filtration. The crystals were dried at 40° C. for 1 hr to give the title compound (116 mg) as a crystalline white powder.

Figure 17:
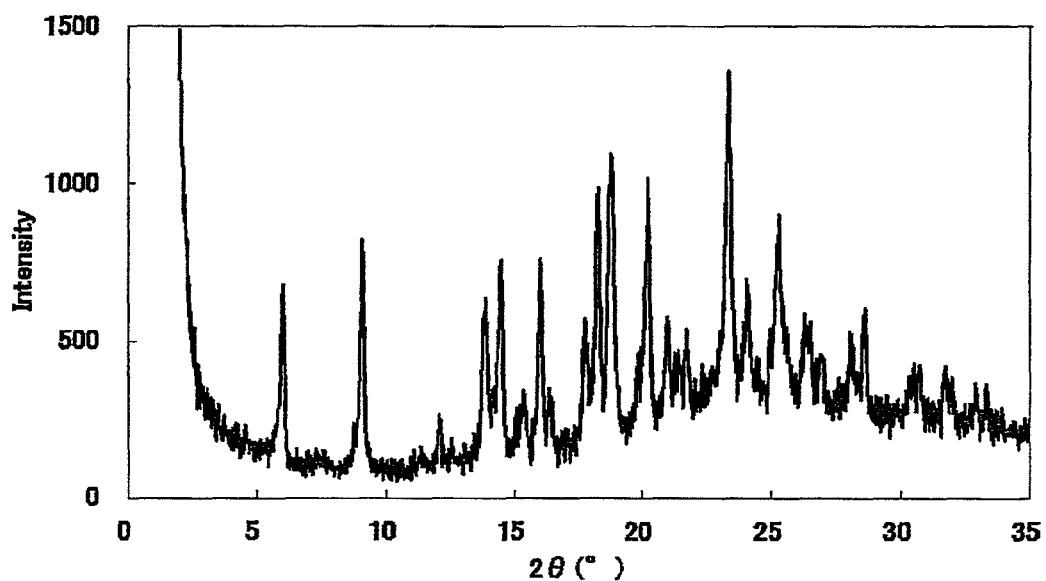
FIG. 17 is a drawing showing the XRD pattern of the present compound 1 fumarate 1-2 hydrate of Example 11.

[XRD (Diffraction Apparatus: RINT2200/Ultima+)]
The XRD pattern is shown in FIG. 17. The characteristic peaks were found at diffraction angles 2θ of about 6.0°, 9.1°, 18.8° and 23.3° (each ±0.2°).

Example 12

Present Compound 1 Hydrobromide

Figure 18:
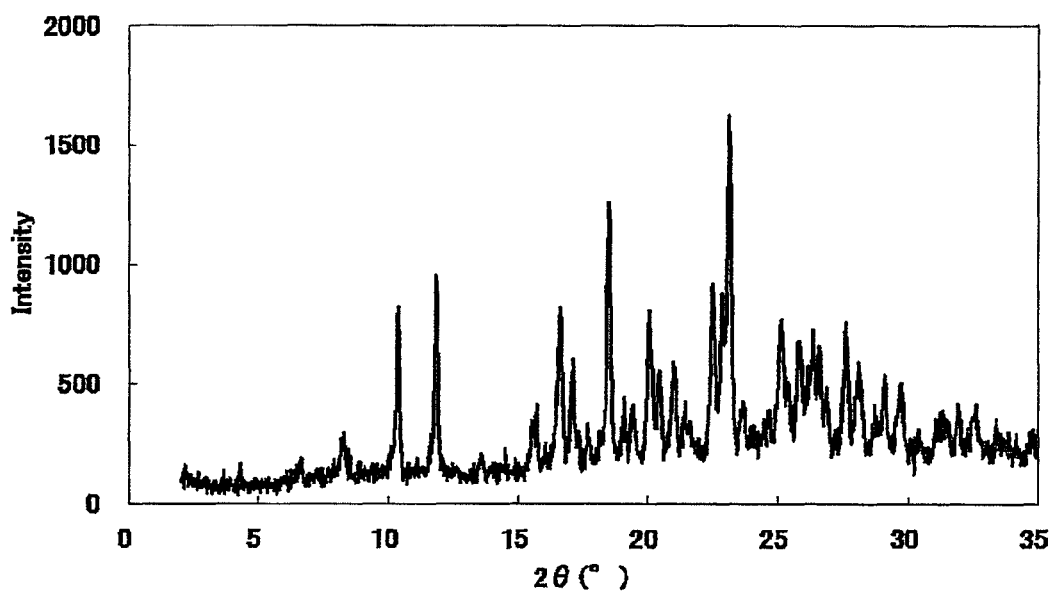
FIG. 18 is a drawing showing the XRD pattern of the present compound 1 hydrobromide of Example 12.

To the present compound (50 mg) was added 90% ethanol solution (0.5 mL), and the mixture was heated to 60° C. While stirring this suspension, a hydrobromic acid-ethanol solution corresponding to 1.2 equivalents was added, and the mixture was completely dissolved and slowly cooled to room temperature. Seed crystals were added thereto, and the mixture was stirred at room temperature for one night and one day. The precipitated crystals were collected by filtration, and air-dried for 10 min to give the title compound (35 mg) as a crystalline white powder.
[XRD (Diffraction Apparatus: RINT2200/Ultima+)]
The XRD pattern is shown in FIG. 18. The characteristic peaks are found at diffraction angles 2θ of about 8.3°, 10.4°, 11.9°, 18.5° and 23.2° (each ±0.2°).

Example 13

Present Compound ½ Citrate

Figure 19:
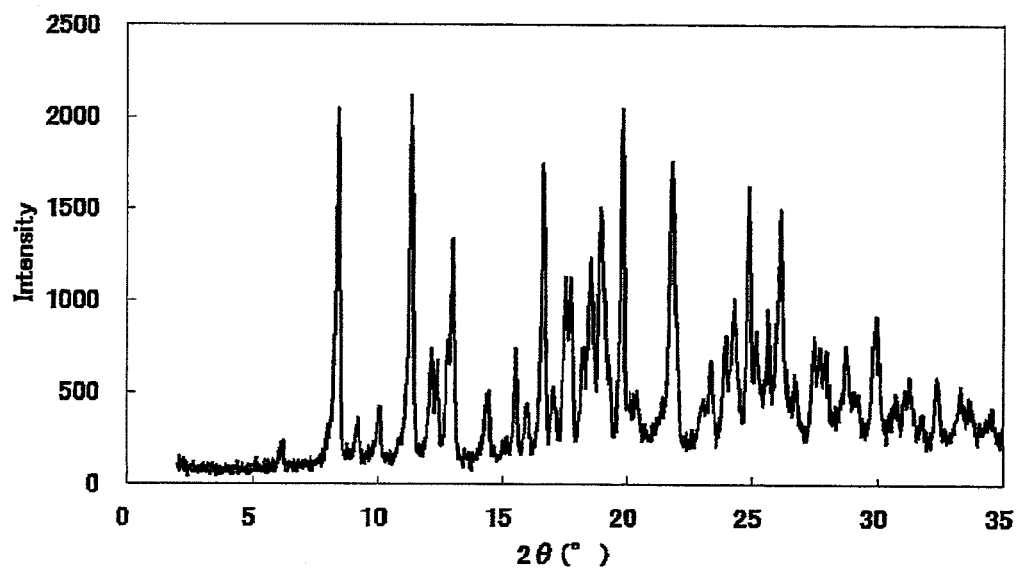
FIG. 19 is a drawing showing the XRD pattern of the present compound ½ citrate of Example 13.

To the present compound (150 mg) was added 80 mM aqueous citric acid solution (2 mL), and the mixture was shaken (200 rpm) at 37° C. for about 24 hr. This was left standing at room temperature for 5 days, and the solid component was collected by filtration to give the title compound (139 mg) as a crystalline white powder.
[XRD (Diffraction Apparatus: RINT2200/Ultima+)]
The XRD pattern is shown in FIG. 19. The characteristic peaks were found at diffraction angles 2θ of about 8.4°, 11.3°, 13.0°, 16.6°, 19.8° and 21.8° (each ±0.2°).

Example 14

Present Compound 1 Citrate

Figure 20:
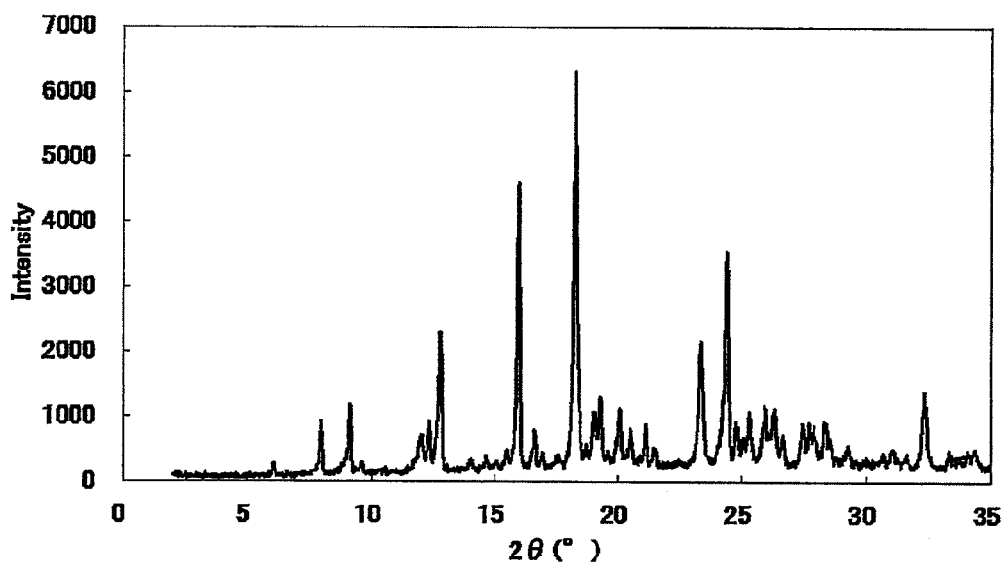
FIG. 20 is a drawing showing the XRD pattern of the present compound 1 citrate of Example 14.

To the present compound ½ citrate (100 mg) was added 1.7M aqueous citric acid solution (1 mL), and the mixture was shaken (200 rpm) at 37° C. for about 24 hr. The solid component was collected by filtration to give the title compound as a crystalline white powder.
[XRD (Diffraction Apparatus: RINT2200/Ultima+)]
The XRD pattern is shown in FIG. 20. The characteristic peaks were found at diffraction angles 2θ of about 8.0°, 9.1°, 16.0°, 18.2° and 24.4° (each ±0.2°).

Example 15

Present Compound ½ DL-Tartrate ½ Hydrate

A suspension of the present compound (440 mg) and methanol (20 ml) was stirred with heating at 80° C., and methanol (10 ml) was added. After complete dissolution, 1M DL-tartaric acid-ethanol solution (2.4 ml, 2.4 equivalents) was added dropwise under stirring with heating at 80° C. The mixture was cooled to room temperature, and stirred as it was for 3 hr. The precipitated crystals were collected by filtration, and dried at 60° C. for 2 hr under vacuum to give the title compound (274.3 mg) as white crystals.

[XRD (Diffraction Apparatus: X'Pert Pro MPD [Condition 1])]

Figure 21:
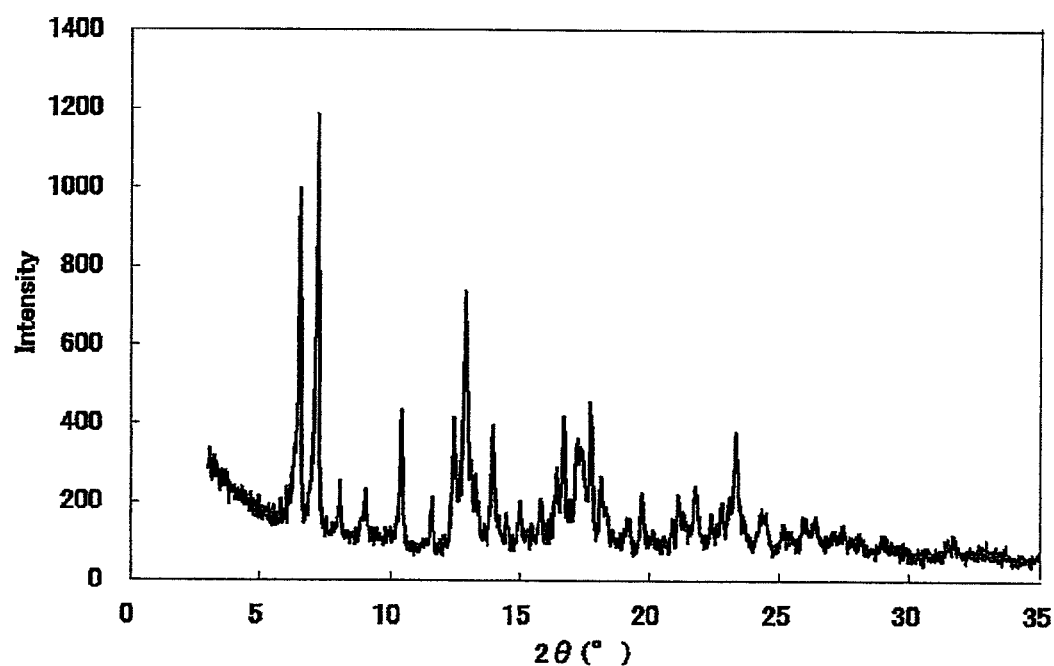
FIG. 21 is a drawing showing the XRD pattern of the present compound 1/20 tartrate ½ hydrate of Example 15.

The measurement was performed after changing the measurement conditions to tube current: 40 mA and tube voltage: 45 kV. The XRD pattern is shown in FIG. 21. The characteristic peaks were found at diffraction angles 2θ of about 6.5°, 7.2°, 10.4°, 12.9° and 13.9° (each ±0.2°).

Example 16

Type I Crystal of the Present Compound

To the present compound (42 g) was added ethanol (150 ml), and the mixture was stirred with heating at 70° C. After complete dissolution, ethyl acetate (600 ml) was added, and the mixture was cooled to room temperature and stirred as it was for one night and one day. The precipitated crystals were collected by filtration and dried under reduced pressure at 60° C. for 10 hr to give the title compound (31 g) as pale-pink crystals.
[XRD (Diffraction Apparatus: RINT2200/Ultima+)]

Figure 22:
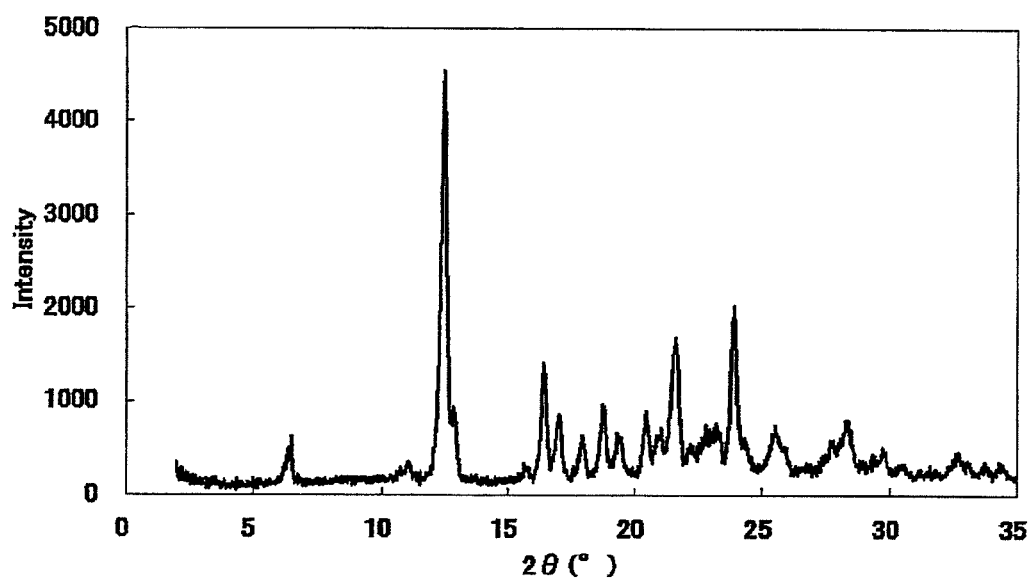
FIG. 22 is a drawing showing the XRD pattern of the crystal of the present compound of Example 16.

The XRD pattern is shown in FIG. 22. The characteristic peaks were found at diffraction angles 2θ of about 6.4°, 12.5°, 12.8°, 16.5°, 18.7°, 21.6° and 23.9° (each ±0.2°).
[DSC]

Figure 23:
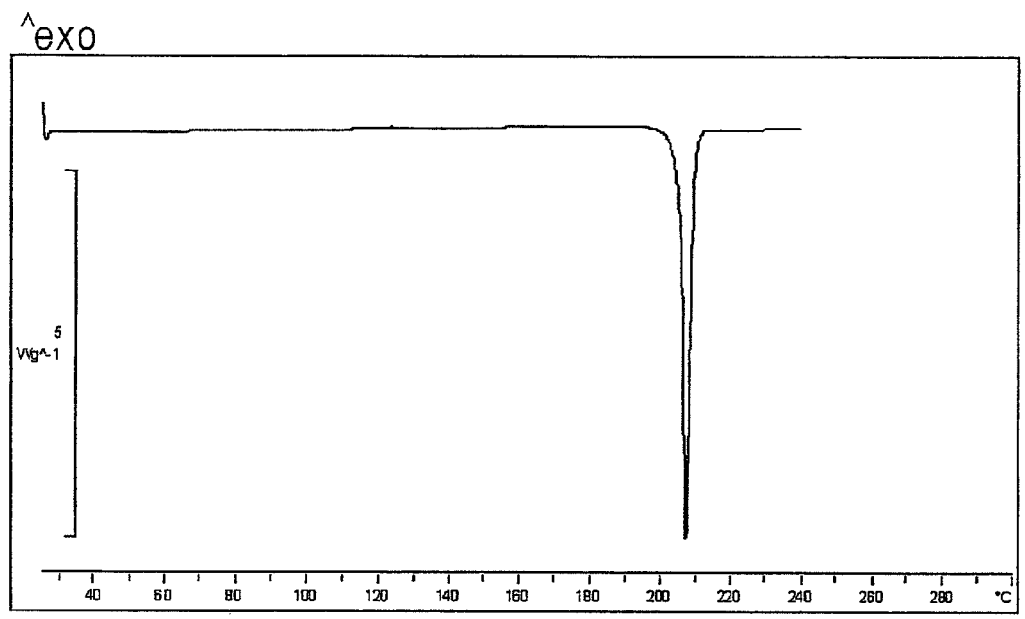
FIG. 23 is a drawing showing the DSC curve of the crystal of the present compound of Example 16.

The melting point (extrapolation starting temperature) was noted at around 206° C. The DSC curve is shown in FIG. 23.

Example 17

Type II Crystal of the Present Compound

To the compound (2 g) obtained in Example 1 was added ethyl acetate (400 ml), and the mixture was heated under reflux. The mixture was completely dissolved, cooled to room temperature, and left standing as it was for one night and one day. The precipitated crystals were collected by filtration and dried under reduced pressure at 60° C. for 5 hr to give the title compound (0.3 g) as white crystals.
[XRD (Diffraction Apparatus: RINT2200/Ultima+)]

Figure 24:
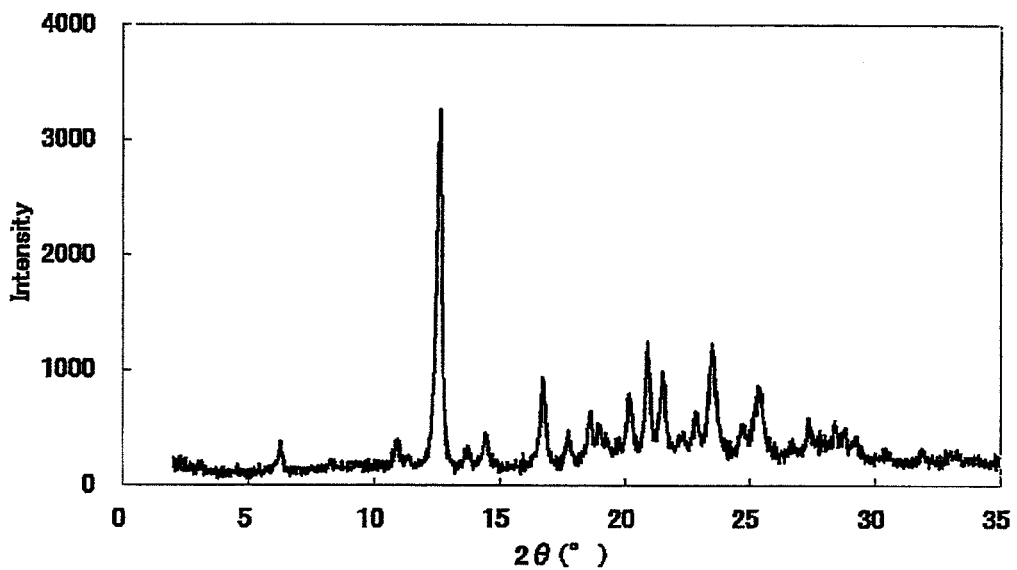
FIG. 24 is a drawing showing the XRD pattern of the crystal of the present compound of Example 17.

The XRD pattern is shown in FIG. 24. The characteristic peaks were found at diffraction angles 2θ of about 6.3°, 12.6°, 13.7°, 14.4°, 16.7°, 20.9° and 23.5° (each ±0.2°).
[DSC]

Figure 25:
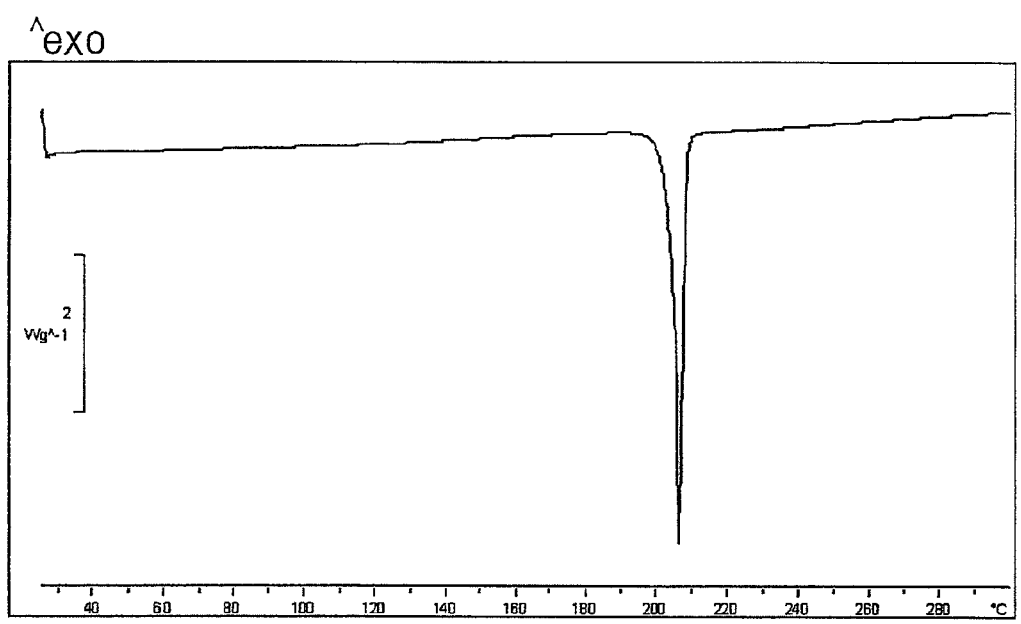
FIG. 25 is a drawing showing the DSC curve of the crystal of the present compound of Example 17.

The melting point (extrapolation starting temperature) was noted at around 204° C. The DSC curve is shown in FIG. 25.

Example 18

Type III Crystal of the Present Compound

To the present compound (25 g) was added ethanol (200 ml) and the mixture was stirred with heating at 70° C. The mixture was completely dissolved and concentrated under reduced pressure to allow precipitation of a solid. The mixture was cooled to room temperature, and left standing as it was for one night and one day. The precipitated crystals were collected by filtration and dried under reduced pressure at 60° C. for 8 hr to give the title compound (20 g) as pale-yellow crystals.
[XRD (Diffraction Apparatus: RINT2200/Ultima+)]

Figure 26:
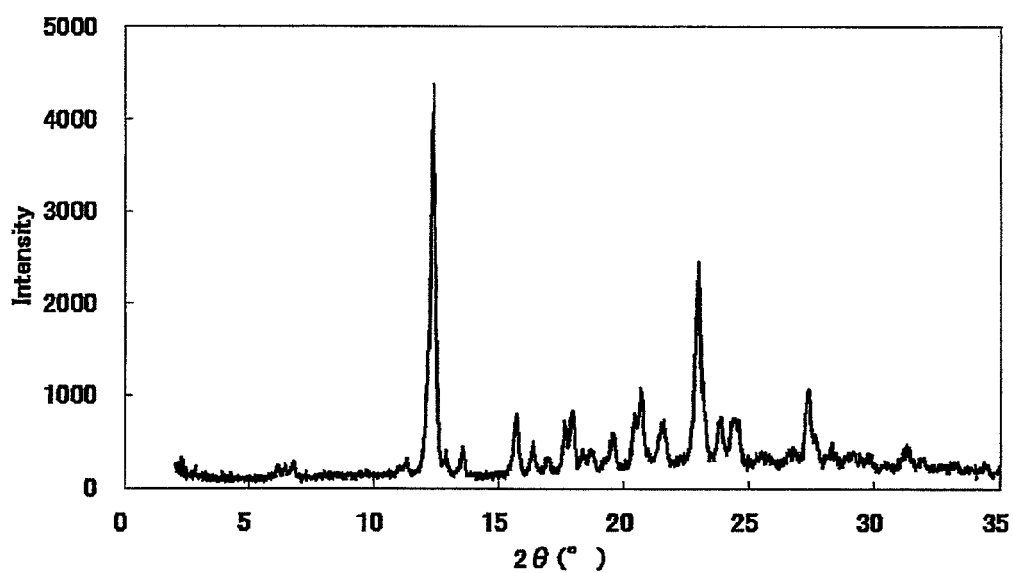
FIG. 26 is a drawing showing the XRD pattern of the crystal of the present compound of Example 18.

The XRD pattern is shown in FIG. 26. The characteristic peaks were found at diffraction angles 2θ of about 6.2°, 6.4°, 6.8°, 12.3°, 15.7° and 23.0° (each ±0.2°).
[DSC]

Figure 27:
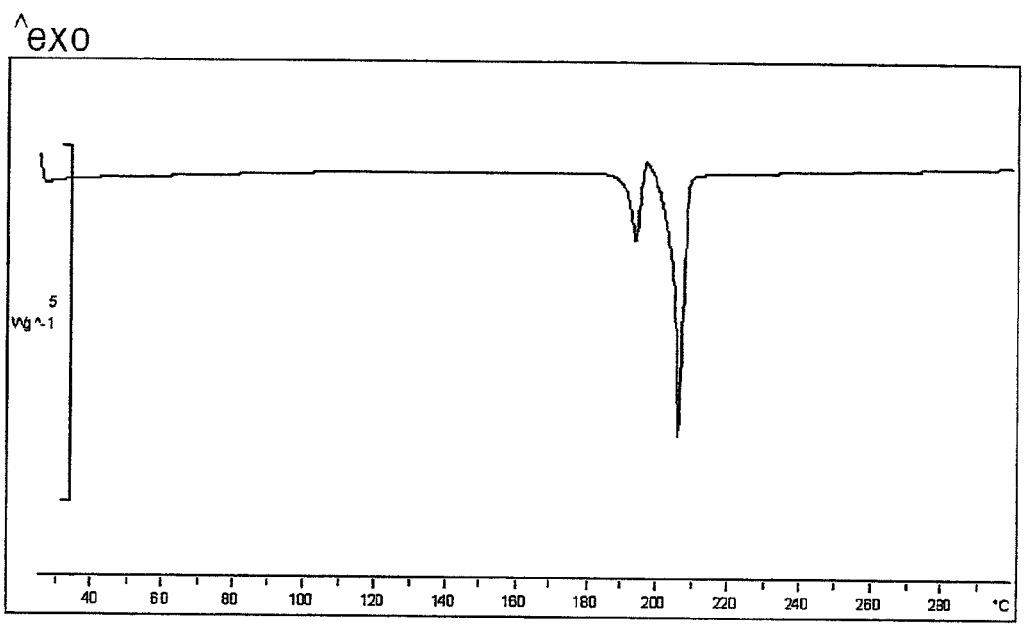
FIG. 27 is a drawing showing the DSC curve of the crystal of the present compound of Example 18.

The melting point (extrapolation starting temperature) was noted at around 191° C. Following the melting peak, an exothermic peak partly overlapping therewith was observed, and thereafter, the second endothermic peak was noted at around 204° C. (extrapolation starting temperature). The DSC curve is shown in FIG. 27.

Example 19

Type IV (1 Hydrate) Crystal of the Present Compound

Type IV (1 hydrate) crystals were obtained according to the following (1)-(2).
(1) A suspension obtained by adding sodium phosphate buffer (pH 6.8, 3 mL) to the hydrochloride 1 hydrate (about 15 mg) of Example 1 was shaken at 37° C. for 24 hr. The solid component of the suspension was rapidly collected by filtration and preserved in a sealed container to give the title compound as white crystals.
(2) To the present compound (5 mg) was added dimethylformamide (250 and the mixture was dissolved by stirring with heating at 60° C. This was filtered with heating, and water (1 mL) was added to the filtrate. The mixture was left standing at 20° C. for one night and one day to give a crystalline white solid.
[XRD (Diffraction Apparatus: RINT2200/Ultima+)]

Figure 28:
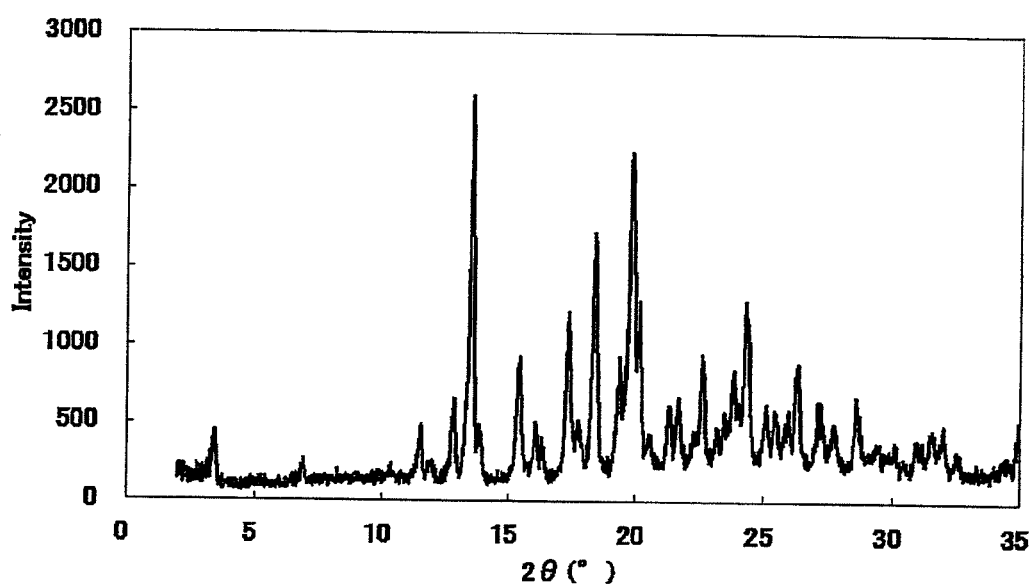
FIG. 28 is a drawing showing the XRD pattern of the present compound 1 hydrate of Example 19.

The XRD pattern is shown in FIG. 28. The characteristic peaks were found at diffraction angles 2θ of about 3.5°, 11.5°, 13.5°, 18.4° and 19.9° (each ±0.2°).

Example 20

Type V Crystals of the Present Compound

The compound (several mg) of Example 19 was dried (for example, dried under reduced pressure at 40° C. for 1 hr) to give the title compound as white crystals.
[XRD (Diffraction Apparatus: RINT2200/Ultima+)]

Figure 29:
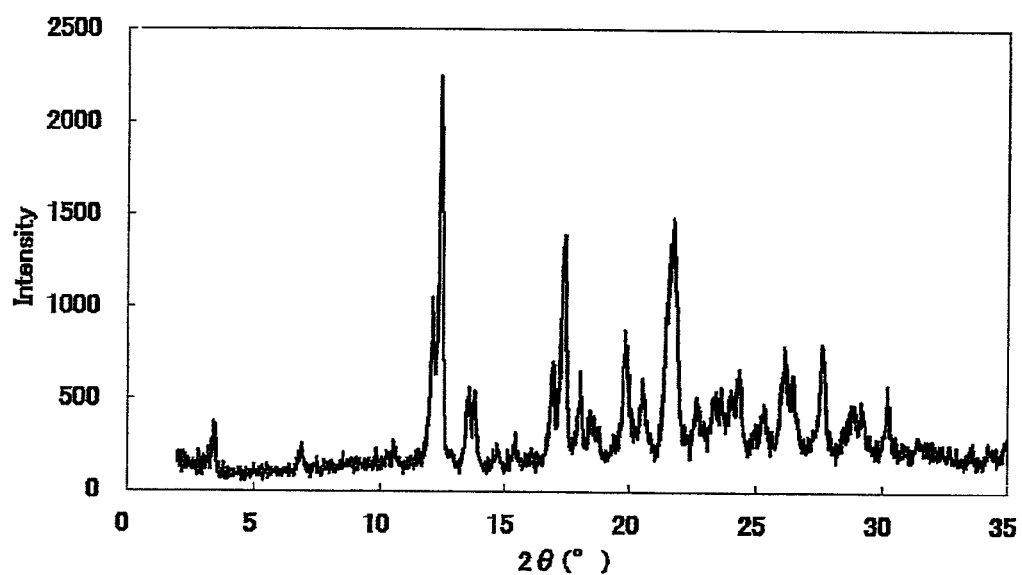
FIG. 29 is a drawing showing the XRD pattern of the crystal of the present compound of Example 20.

The XRD pattern is shown in FIG. 29. The characteristic peaks were found at diffraction angles 2θ of about 3.4°, 6.9°, 12.1°, 12.4°, 17.4° and 21.7° (each ±0.2°).
[DSC]

Figure 30:
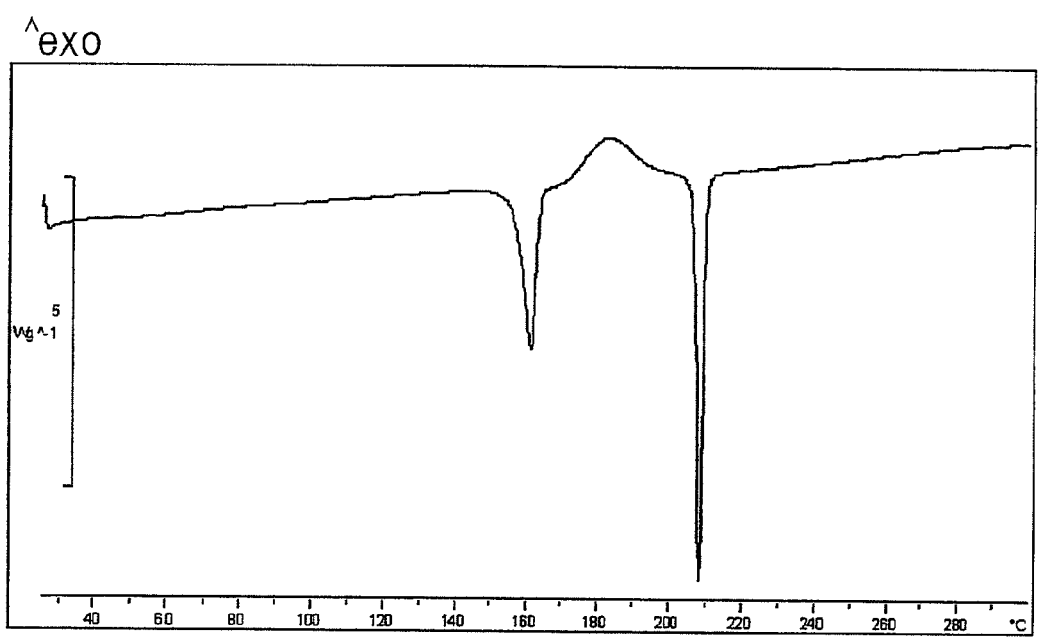
FIG. 30 is a drawing showing the DSC curve of the crystal of the present compound of Example 20.

The melting point (extrapolation starting temperature) was noted at around 157° C. Following the melting peak, an exothermic peak was observed at around 172° C. (extrapolation starting temperature), and thereafter, the second endothermic peak was noted at around 207° C. (extrapolation starting temperature). The DSC curve is shown in FIG. 30.

Experimental Example 1

Water Adsorption Measurement

The water adsorption measurement, which becomes an index of hygroscopicity, was performed using a DVS-1 type water adsorption apparatus (manufactured by SMS) under the following conditions. Using a sample (about 6-12 mg), the relative humidity was changed within the relative humidity range of 0% to 95%. The weight change was recorded for each predetermined relative humidity, and converted to the amount of change (%) based on the weight at relative humidity 0%. The 1 hydrochloride 1 hydrate of Example 1 was a hydrate having extremely stable crystallization water, and the weight decrease did not reach 0 even when it was left standing at relative humidity 0% RH for 15 hr. As to this compound, the zero point was amended based on the moisture value of the sample measured by the Karl Fischer's method, and the weight change was converted to the amount of change (%).

Figure 31:
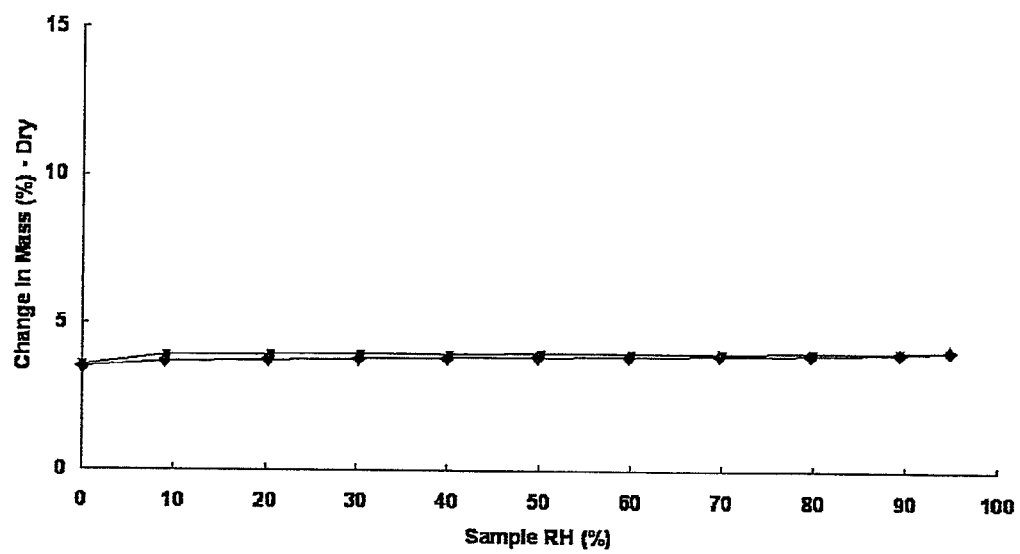
FIG. 31 is a drawing showing the results of water adsorption measurement of the present compound 1 hydrochloride 1 hydrate of Example 1.
Figure 32:
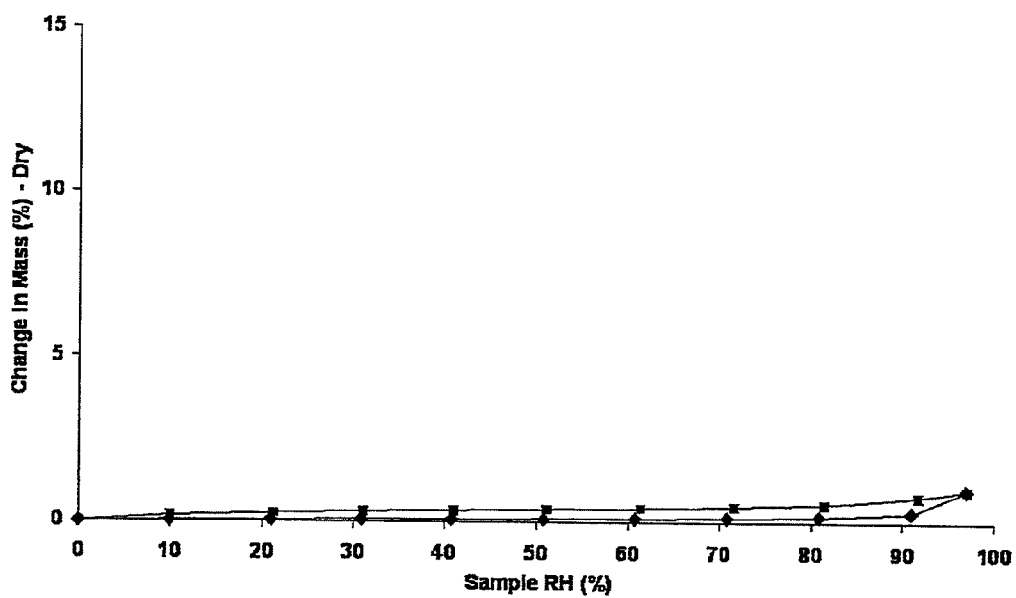
FIG. 32 is a drawing showing the results of water adsorption measurement of the present compound 1 hydrochloride of Example 2.
Figure 33:
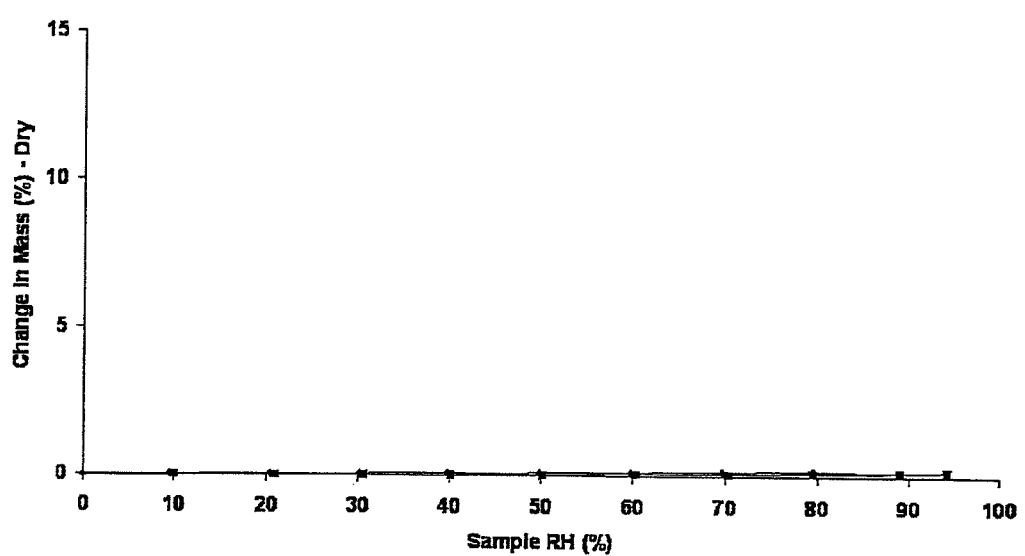
FIG. 33 is a drawing showing the results of water adsorption measurement of the present compound 1 methanesulfonate of Example 6.

The water adsorption measurement results of the 1 hydrochloride 1 hydrate of Example 1, the 1 hydrochloride anhydride of Example 2, and the 1 methanesulfonate anhydride of Example 6 are each as shown in FIG. 31, FIG. 32 and FIG. 33, and showed a weight increase of 0.2%, 0.2% and 0.4%, respectively. It was clarified that these compounds showed small weight change due to the humidity change, and had a desirable form as a drug substance of pharmaceutical products.

On the other hand, the ½ fumarate 3/2 hydrate of Example 10, and the 1 methanesulfonate 3 hydrate of Example 8 showed a weight increase of 1.3% and 2.0%, respectively, due to the moisture absorption. In addition, all of the 1 hydrochloride 2-3 hydrate of Example 3, the 1 methanesulfonate ½-1 hydrate of Example 7, the 1 fumarate 1-2 hydrate of Example 11, the ½ citrate of Example 13, the 1 citrate of Example 14, and the ½ tartrate ½ hydrate of Example 15 showed a weight increase of not less than 4% due to the moisture absorption.

Experimental Example 2

Solubility in Water

The solubility of the obtained compounds in water at 37° C. was measured under the following conditions. An adequate amount of each sample was taken, water was added to each sample, and the mixture was shaken at 37° C. for 4 hr. The supernatant was filtered through a filter, and diluted with a mixed solution of TFA/acetonitrile/water=(0.05:30:70) as necessary to give a sample solution. The concentration (mg/ml) of the sample solution was measured by high performance liquid chromatography (HPLC) with a calibration curve method, and taken as the solubility in water at 37° C.

HPLC Analysis Conditions
   apparatus: HPLC System Class-VP (SHIMADZU Corporation)
   detector: photodiode array detector
   measurement wavelength range: 200-370 nm
   fixed wavelength: 220 nm
   column: Inertsil ODS-3V (4.6 mm$_9$×150 mm)
   column temperature: 40° C.
   mobile phase: SOLUTION A 0.05% aqueous trifluoroacetic acid solution
     SOLUTION B 0.05% trifluoroacetic acid-acetonitrile solution
   A:B=70:30 (Isocratic Elution)
   flow rate: 1.0 mL/min The solubility of each sample in water is shown below.
Example 16: 0.01 mg/ml
Example 17: 0.01 mg/ml
Example 6: >2 mg/ml
Example 1: >2 mg/ml
Example 10: 0.3 mg/ml

INDUSTRIAL APPLICABILITY

The present invention can provide a stable form of (R)-2-{3-[1-(acenaphthen-1-yl)piperidin-4-yl]-2,3-dihydro-2-oxo-benzimidazol-1-yl}-N-methylacetamide, which is free of problems of water adsorption and the like, has superior water solubility, and has superior water solubility.

This application is based on JP 2008-235846 filed in Japan, the contents of which are encompassed in full herein.

The invention claimed is:
1. (R)-2-{3-[1-(acenaphthen-1-yl)piperidin-4-yl]-2,3-dihydro-2-oxo-benzimidazol-1-yl}-N-methylacetamide 1 hydrochloride 1 hydrate showing peaks at diffraction angles 2θ of about 5.6°, 16.2°, 19.0°, 20.1° and 24.9° (each ±0.2°) in powder X-ray diffraction spectrum.

* * * * *